US00RE47569E

(19) United States
(12) Reissued Patent
Shimizu et al.

(10) Patent Number: US RE47,569 E
(45) **Date of Reissued Patent: *Aug. 13, 2019**

(54) PROCESS FOR PRODUCING ACETIC ACID

(71) Applicant: DAICEL CORPORATION, Osaka-shi, Osaka (JP)

(72) Inventors: Masahiko Shimizu, Himeji (JP); Ryuji Saito, Himeji (JP); Hiroyuki Miura, Himeji (JP)

(73) Assignee: DAICEL CORPORATION, Osaka-Shi (JP)

( * ) Notice: This patent is subject to a terminal disclaimer.

(21) Appl. No.: 16/026,736

(22) Filed: Jul. 3, 2018

Related U.S. Patent Documents

Reissue of:
(64) Patent No.: 9,162,958
Issued: Oct. 20, 2015
Appl. No.: 13/995,102
PCT Filed: Dec. 1, 2011
PCT No.: PCT/JP2011/077846
§ 371 (c)(1),
(2) Date: Jun. 17, 2013
PCT Pub. No.: WO2012/081418
PCT Pub. Date: Jun. 21, 2012

U.S. Applications:
(63) Continuation of application No. 15/664,076, filed on Jul. 31, 2017, now Pat. No. Re. 46,999, which is an application for the reissue of Pat. No. 9,162,958.

(30) Foreign Application Priority Data

Dec. 15, 2010 (JP) ..... 2010-279799

(51) Int. Cl.
*C07C 51/12* (2006.01)
*C07C 51/44* (2006.01)

(52) U.S. Cl.
CPC ..... *C07C 51/12* (2013.01); *C07C 51/44* (2013.01)

(58) Field of Classification Search
CPC ..... C07C 51/12; C07C 51/44
See application file for complete search history.

(56) References Cited

U.S. PATENT DOCUMENTS

| | | | | |
|---|---|---|---|---|
| 3,335,179 | A | 8/1967 | Null et al. | |
| 3,769,329 | A | 10/1973 | Paulik et al | |
| 5,001,259 | A | 3/1991 | Smith et al. | |
| 5,144,068 | A | 9/1992 | Smith et al. | |
| 5,625,095 | A | 4/1997 | Miura et al. | |
| 6,143,930 | A | 11/2000 | Singh et al. | |
| 6,339,171 | B1 | 1/2002 | Singh et al. | |
| RE46,999 | E * | 8/2018 | Shimizu | C07C 51/12 |
| 2003/0135070 | A1 | 7/2003 | Picard et al. | |
| 2005/0197506 | A1 | 9/2005 | Scates et al. | |
| 2006/0247466 | A1 | 11/2006 | Zinobile et al. | |
| 2009/0036710 | A1 | 2/2009 | Miura et al. | |
| 2009/0270650 | A1 | 10/2009 | Patt | |

FOREIGN PATENT DOCUMENTS

| | | | |
|---|---|---|---|
| JP | 8-12612 | A | 1/1996 |
| JP | 8-67650 | A | 3/1996 |
| JP | 2000-72712 | A | 3/2000 |
| JP | 3581725 | B2 | 10/2004 |
| JP | 2005-515227 | A | 5/2005 |
| JP | 2005-289936 | A | 10/2005 |
| JP | 2007-526308 | A | 9/2007 |
| WO | WO 03/059860 | A2 | 7/2003 |
| WO | WO 2005/085163 | A1 | 9/2005 |
| WO | WO 2005/087698 | A1 | 9/2005 |
| WO | WO 2008/016502 | A2 | 2/2008 |

OTHER PUBLICATIONS

Schillmoller, "Selection and use of stainless steels and nickel-bearing alloys in organic acids," NiDI Technical Series No. 10 063. (Year: 1992).*
Hagen, Industrial Catalysis, Wiley-VCH Verlag GmbH & Co. KGaA, pp. 65-67 . (Year: 2006).*
"Sandvik duplex stainless steel" brochure. (Year: 2009).*
International Search Report issued in PCT/JP2011/077846, dated Mar. 19, 2012, with English translation.
Translation of International Preliminary Report on Patentability and Written Opinion issued in PCT/JP2011/077846, dated Jun. 18, 2013.
Amendment Under 37 CFR 1.111 filed Jun. 11, 2015, in U.S. Appl. No. 13/995,102.
Certified English translation of JP 2000-27212 A1 (Mar. 7, 2000).
Curriculum Vitae of Ronnie M. Hanes, IPR2017-00164, submitted Oct. 31, 2016.
Declaration of Dr. Ronnie Michael Hanes under 37 CFR 1.68, IPR2017-00164, dated Oct. 31, 2016.
European Search Report dated Nov. 9, 2015, issued in European Patent Application No. 11848683.6.
Gambale, D., "Choosing Specialty Metals for Corrosion-Sensitive Equipment," Amer. Inst. Chem. Eng'g. (Jul. 2010), pp. 62-66.

(Continued)

*Primary Examiner* — Alan D Diamond
(74) *Attorney, Agent, or Firm* — Birch, Stewart, Kolasch & Birch, LLP

(57) ABSTRACT

Acetic acid is produced while inhibiting increased concentrations of hydrogen iodide and acetic acid in an acetaldehyde distillation column.

A production process of acetic acid comprises a step for allowing methanol to react with carbon monoxide; a step for feeding a flasher with the reaction mixture to separate a volatile component (2A) and a low-volatile component (2B); a step for feeding a distillation column with the volatile component (2A), and separating an overhead (3A) containing methyl iodide, acetic acid, methyl acetate, water, acetaldehyde, and hydrogen iodide, and a stream (3B) containing acetic acid to collect acetic acid; and a separation step for feeding an acetaldehyde distillation column with at least part of the overhead (3A) and separating a liquid object to be treated containing the overhead (3A) into a lower boiling point component (4A) containing acetaldehyde and a higher boiling point component (4B); wherein, in the separation step, the liquid object contains methanol and/or dimethyl ether in a concentration of 0.1 to 50% by weight is subjected to distillation.

8 Claims, 2 Drawing Sheets

(56) References Cited

OTHER PUBLICATIONS

Gerrard, W., Solubility of Gases and Liquids, p. 130 (1976).
Institution Decision, Paper No. 7, IPR2017-00164, dated May 8, 2017.
Non-Final Office Action dated Mar. 11, 2015, in U.S. Appl. No. 13/995,102.
Notice of Allowance dated Jul. 6, 2015, in U.S. Appl. No. 13/995,102.
Petition for Inter Partes Review, IPR2017-00164, filed Oct. 31, 2016.
Roth, J. F., "The Production of Acetic Acid: Rhodium Catalysed Carbonylation of Methanol," Platinum Metals Rev. (1975), vol. 19, No. 1, pp. 12-14.
The Merck Index, An Encyclopedia of Chemicals, Drugs, and Biologicals, 13th Edition, p. 858 (2001).
Torrence, P. "Chapter 2.1.2 Carbonylations," Applied Homogenous Catalysis with Organometallic Compounds, Ed. 2, pp. 104-136.
Machine translation of JP 2000-72712.*
Machine translation of JP 2005-289936.*

* cited by examiner

PROCESS FOR PRODUCING ACETIC ACID

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 9,162,958. The reissue applications are application Ser. No. 16/026,736 (the present application) and Ser. No. 15/664,076, all of which are reissues of U.S. Pat. No. 9,162,958.*

*CROSS REFERENCE TO RELATED APPLICATIONS*

*This application is a Reissue Continuation of U.S. application Ser. No. 15/664,076 filed on Jul. 31, 2017, which is a Reissue Application of U.S. application Ser. No. 13/995,102 filed on Jun. 17, 2013, and issued as U.S. Pat. No. 9,162,958 B2 on Oct. 20, 2015, which is a 35 U.S.C. § 371 National Phase of PCT International Application No. PCT/JP2011/077846 filed Dec. 1, 2011, which claims priority on Japanese Patent Application No. 2010-279799 filed Dec. 15, 2010. All of the above-referenced applications are incorporated by reference into the present application.*

TECHNICAL FIELD

The present invention relates to a process for producing acetic acid while efficiently inhibiting an increase in concentration of hydrogen iodide (particularly, hydrogen iodide and acetic acid) in an acetaldehyde distillation column.

BACKGROUND ART

Various industrial production processes of acetic acid have been known. Among others, an industrially excellent process includes a process which comprises continuously allowing methanol to react with carbon monoxide with the use of a metal catalyst (such as a rhodium catalyst) and methyl iodide in the presence of water to give acetic acid. Moreover, recently improvement in reaction conditions and catalysts was investigated, and an industrial process for producing acetic acid with a highly efficient production has been developed by addition of a catalyst stabilizer (such as an iodide salt) and the reaction under a low water content condition compared with the conventional condition.

In this process, a volatile component is separated when acetic acid is separated from a liquid reaction mixture by distillation. The volatile component contains a useful component such as methyl iodide, while the component is a liquid component containing acetaldehyde. Therefore, the volatile component is collected or recycled to the reaction system after acetaldehyde is separated by distillation (or condensation). The volatile component contains an acidic component (such as hydrogen iodide or acetic acid) in addition to methyl iodide, acetaldehyde, water, and methyl acetate. When hydrogen iodide or acetic acid is condensed (or produced) in an acetaldehyde distillation column under a distillation condition (such as an applied pressure or a high temperature), the corrosion of the acetaldehyde distillation column may be precipitated. Moreover, when the solution containing methyl iodide is subjected to distillation and then the separated fraction and/or the residue are recycled to the reaction system, the corrosion of a pump for recycling (recycle pump) or a line for recycling may be precipitated. Therefore, it is preferable that the concentration of the acidic component (such as hydrogen iodide or acetic acid) in the distillation column for separating acetaldehyde be reduced.

Japanese Patent No. 3581725 (JP-3581725B, Patent Document 1) discloses a recycling process which comprises carbonylating methanol and/or methyl acetate in a reaction medium containing a group 8 metal catalyst of the Periodic Table and methyl iodide; separating a volatile phase and a low-volatile phase from the carbonylation product, where the volatile phase contains the product, unreacted methanol and/or methyl acetate, and methyl iodide, and the low-volatile phase contains the group 8 metal catalyst; distilling the volatile phase to give an overhead containing the product, the unreacted methanol and/or methyl acetate, and methyl iodide; and recycling the overhead to the carbonylation reactor; wherein the overhead is a mixture containing acetaldehyde and methyl iodide, the overhead is recycled to the reactor after distillation of the overhead in the presence of methanol at a column top temperature of less than 55° C. and a reflux tank temperature of less than 25° C. and dissolution of acetaldehyde produced in a paraldehyde or metaldehyde form in a mixed solution containing methyl iodide and methanol in a weight ratio (methyl iodide/methanol) of 5/4 to 1/2 as a composition of a bottom fraction of the distillation column for removal or separation.

Incidentally, according to the process described in the document, use of methanol in the distillation column aims at dissolution of paraldehyde or metaldehyde and is not intended for inhibition of hydrogen iodide production. Moreover, the process described in the document needs methanol 0.8 to 2 times as much as the weight of highly rich methyl iodide contained in the overhead, and it is necessary to treat a large quantity of a liquid object to be treated composed of the total amount the overhead and methanol. Thus it is necessary to use a distillation column having a large column diameter, which is not economical.

WO2008/016502 publication (WO2008/016502, Patent Document 2) discloses a process for decreasing an aldehyde impurity from an acetic acid stream, which comprises allowing an acetic acid stream containing an aldehyde impurity to react with a hydroxy compound (such as glycol, polyol, or a $C_{4-10}$ alcohol) to convert the aldehyde impurity into an acetal, and separating the acetal. Specifically, the document discloses the following recycling technique: an overhead containing methyl iodide, methyl acetate, acetic acid, water, and an aldehyde impurity is liquefied in a decanter, 5 to 50% of the resulting heavy phase (organic phase), which contains methyl iodide and the aldehyde impurity, is treated with a hydroxy compound in a ratio of 1 to 10 equivalents of the hydroxy compound relative to the aldehyde impurity and then distilled to separate an acetal fraction and a methyl iodide fraction, and the acetal fraction is wasted and methyl iodide is recycled to the heavy phase in the decanter or the carbonylation reaction. The document also discloses that methyl iodide to be used for the reaction can be produced by adding hydrogen iodide to a carbonyl reactor. Thus the document intends the hydroxy compound is used for conversion of an aldehyde into an acetal, and an acidic ion exchange resin is used for acetalation, and the document never intends the decrease in hydrogen iodide or acetic acid.

Japanese Patent Application laid-Open No. 2007-526308 (JP-2007-526308A, Patent Document 3) discloses a process for producing acetic acid, comprising the steps of: (a)

reacting carbon monoxide with at least one reactant selected from the group consisting of methanol, methyl acetate, methyl formate, dimethyl ether and mixtures thereof in a reaction medium comprising water, methyl iodide, and a catalyst to produce a reaction product comprising acetic acid; (b) performing a vapor-liquid separation on the reaction product to provide a volatile phase comprising acetic acid, water, and methyl iodide and a less-volatile phase comprising the catalyst; (c) distilling said volatile phase to produce a purified acetic acid product and a first overhead comprising water, methyl acetate, and methyl iodide; (d) phase-separating the first overhead to provide a first liquid phase comprising water and a second liquid phase comprising methyl iodide; (e) adding dimethyl ether to the process in an amount effective to enhance separation of the first overhead to form the first and second liquid phases; and removing acetaldehyde from at least one of the first and second liquid phases, wherein the dimethyl ether is added to a stream associated with the acetaldehyde removal step. According to the document, dimethyl ether is used as a component to easily separate the first and second liquid phases, and the decrease in hydrogen iodide or acetic acid is not intended. Moreover, the document is silent on an amount to be added of dimethyl ether.

Japanese Patent Application Laid-Open No. 2000-72712 (JP-2000-72712A, Patent Document 4) discloses a process for producing acetic acid, which comprises a first step for allowing carbon monoxide to react with methanol, dimethyl ether, or methyl acetate in the presence of a rhodium catalyst, an iodide salt, and methyl iodide; a second step for distilling the liquid reaction mixture obtained in the first step to separate a high-volatile phase containing a carbonyl compound and a low-volatile phase; a third step for distilling the high-volatile phase containing the carbonyl compound obtained in the second step to separate a product containing acetic acid and an impurity containing the carbonyl compound; a fourth step for allowing the impurity containing the carbonyl compound obtained in the third step to contact with water to separate an organic phase containing an alkyl iodide and an aqueous phase containing the carbonyl compound; and a fifth step for sending back the organic phase obtained in the fourth step to the reaction step; wherein the contact of the impurity containing the carbonyl compound with water in the fourth step is carried out at 30 to 60° C. The document discloses that the process may comprise a 3b step, between the third step and the fourth step, for distilling the impurity containing the carbonyl compound obtained in third step by a multistage distillation column and that methanol 0.1 to 55 mol times as much as the iodide ion existing in the multistage distillation column may be fed in the distillation.

Moreover, the document discloses that (i) in the 3b step, hydrogen iodide produced by the reaction of methyl iodide with water sometimes causes corrosion of a metal used for the distillation column, (ii) since the reaction is an equilibrium reaction, addition of methanol to the distillation column inhibits the production of hydrogen iodide and then the metal corrosion, and (iii) since methanol is a lower boiling point component and the azeotropic temperature of hydrogen iodide and water is 127° C., methanol is preferably added at the bottom or vicinity thereof of the distillation column. Further, the document discloses in Examples that, in the 3b step, methanol 10 mol times as much as the iodide ion concentration in a 80-plate distillation column is added at 10 g/hr at a bottom gaseous phase in the distillation column, and the distillation is continued at 82° C., and accordingly the concentration of the iodide ion in the multistage distillation column was not more than 1 ppm; and that addition of a predetermined quantity of methanol to a liquid mixture as a model solution containing methyl iodide, water, and hydrogen iodide reduced the concentration of the iodide ion.

In the process described in the document, however, a liquid mixture containing only methyl iodide, water, and hydrogen iodide is used as the model solution, and the effect of methanol added on a model solution containing acetic acid and methyl acetate is not investigated. Moreover, the feeding of methanol about 0.1 to 55 mol times as much as the amount of the iodide ion is insufficient to decrease the acid concentration in an actual process solution containing not only hydrogen iodide but also acetic acid or methyl acetate and having a complicated composition. Further, according to the process described in the document, since methanol is added to the bottom gaseous phase, it is difficult to efficiently inhibit the corrosion of the whole distillation column. Thus the process is not efficient.

RELATED ART DOCUMENTS

Patent Documents

Patent Document 1: JP-3581725B (Claims)
Patent Document 2: WO2008/016502 (Claims, page 4, lines 22 to 28, page 5, line 30 to page 7, line 12, and Examples)
Patent Document 3: JP-2007-526308A (Claims 1 and 4)
Patent Document 4: JP-2000-72712A (Claims, Paragraph Nos. [0028] and [0029], and Examples)

SUMMARY OF THE INVENTION

Problems to be Solved by the Invention

It is therefore an object of the present invention to provide a process for producing acetic acid while efficiently inhibiting (or preventing) an increase in concentration of hydrogen iodide (particularly, hydrogen iodide and acetic acid) in an acetaldehyde distillation column.

It is another object of the present invention to provide a process for producing acetic acid, the process inhibiting (or preventing) corrosion of an acetaldehyde distillation column.

It is still another object of the present invention to provide process for producing acetic acid, the process efficiently separating acetaldehyde even using an acetaldehyde distillation column made of an inexpensive material.

It is a further object of the present invention to provide a process for stably producing acetic acid (acetic acid with a high purity) while efficiently removing acetaldehyde.

It is another object of the present invention to provide a process for producing acetic acid while recycling methyl iodide as a catalyst with a high efficiency.

Means to Solve the Problems

The inventors of the present invention investigated a method for reducing a concentration of hydrogen iodide in an acetaldehyde distillation column with respect to a process which comprises subjecting methanol to a carbonylation reaction with a catalyst system containing a metal catalyst, a halide salt, and methyl iodide, separating a stream containing a product acetic acid from the resulting volatile component, and removing acetaldehyde from the resulting lower boiling point component (overhead) containing methyl iodide and acetaldehyde by distillation (and further efficiently collecting a useful component such as methyl iodide to recycle the useful component to the reaction system); and found that the concentration of hydrogen iodide cannot be reduced sufficiently by simple addition of methanol to the acetaldehyde distillation column, which is made according to only concentration of the iodide ion as described in JP-2000-72712A.

Specifically, according to JP-2000-72712A, hydrogen iodide can be decreased by adding methanol in consideration of the following equilibrium reaction (1) in which hydrogen iodide is involved:

$$CH_3I+H_2O \Leftrightarrow CH_3OH+HI \quad (1)$$

However, since the overhead contains acetic acid, methyl acetate, and water in addition to methyl iodide and hydrogen iodide, a plurality of equilibrium reactions including the following reactions in which methanol participates occurs other than the reaction (1). Thus the reaction system is highly complicated.

$$CH_3COOH+CH_3OH \Leftrightarrow CH_3COOCH_3+H_2O$$

$$CH_3I+CH_3COOH \Leftrightarrow CH_3COOCH_3+HI$$

Accordingly, in the system containing acetic acid, methyl acetate, and others, it is difficult to reduce the concentration of hydrogen iodide even if the reaction (1) is simply noticed. Further, not only hydrogen iodide but also acetic acid is also an acidic component, and it is preferable acetic acid be decreased because acetic acid is a caused factor of the corrosion of the acetaldehyde distillation column. From the points of view of the reduction of the concentration of hydrogen iodide (further, the reduction the concentration of acetic acid) and an efficient collection of methyl iodide, it is further found that the consideration of only the reaction (1) does not go far enough. Further, use of a large quantity of methanol not only requires a large acetaldehyde distillation column but also significantly reduces the process efficiency due to a large quantity of a process solution to be distilled.

Accordingly, the inventors of the present invention made intensive studies to achieve the above objects and finally found that, in an acetaldehyde distillation column, distillation of a process solution which comprises an overhead containing acetic acid and methyl acetate in addition to methyl iodide, acetaldehyde, and hydrogen iodide and a specific quantity of methanol and/or dimethyl ether added to the overhead efficiently inhibits or prevents an increase in a concentration of hydrogen iodide (further a concentration of acetic acid) in the acetaldehyde distillation column; that the corrosion of the acetaldehyde distillation column is prevented or inhibited, and use of an inexpensive material for the acetaldehyde distillation column reduces the production process cost of acetic acid; and that the separation of acetaldehyde (and collection of methyl iodide) is efficiently performed while inhibiting an increase in concentration of hydrogen iodide (and acetic acid). The present invention was accomplished based on the above findings.

That is, the process of the present invention includes a process for producing acetic acid, the process comprising a reaction step for continuously allowing methanol to react with carbon monoxide in the presence of a catalyst system comprising a metal catalyst, a halide salt, and methyl iodide in a carbonylation reactor; a flash evaporation step for continuously feeding a flasher with a reaction mixture from the reactor to separate a volatile component (2A) containing product acetic acid, methyl acetate, methyl iodide and water, and a low-volatile component (2B) containing the metal catalyst and the halide salt; an acetic acid collection step for feeding a distillation column with the volatile component (2A), and separating an overhead (3A) containing methyl iodide, acetic acid, methyl acetate, water, by-product acetaldehyde, and hydrogen iodide, and a stream (3B) containing acetic acid to collect acetic acid; and an acetaldehyde separation step for feeding an acetaldehyde distillation column (removal column or separation column) with the condensed overhead (3A) (part or all of overhead (3A)) and distilling a liquid object to be treated containing the overhead (3A) (or a condensed component or condensate in the overhead (3A)) to separate a lower boiling point component (4A) containing acetaldehyde and a higher boiling point component (4B); wherein, in the acetaldehyde separation step, the liquid object containing at least one methanol source selected from the group consisting of methanol and dimethyl ether in a concentration of 0.1 to 50% by weight is subjected to distillation.

In the process, in the liquid object, the proportion of methyl iodide may be about 1 to 98% by weight (e.g., about 1 to 95% by weight), the proportion of methyl acetate may be about 0.5 to 50% by weight (e.g., about 0.5 to 30% by weight), the proportion of acetic acid may be about 0.2 to 50% by weight, the proportion of water may be about 0.1 to 90% by weight, and the proportion of hydrogen iodide may be about 1 to 1000 ppm (e.g., about 1 to 300 ppm) on the basis of weight.

In the process, the concentration of the methanol source in the liquid object may be about 0.1 to 50% by weight (e.g., about 0.2 to 50% by weight), and may be about 1 to 30% by weight (e.g., about 2 to 25% by weight). Moreover, in the process, in the liquid object, the concentration of acetic acid may be about 0.3 to 50% by weight, the ratio of the methanol source (in terms of methanol) may be about 0.1 to 40 mol relative to 1 mol of a total amount of acetic acid and hydrogen iodide. Further, in the process, the ratio of the methanol source (in terms of methanol) in the liquid object may be not less than 80 mol (e.g., not less than 200 mol) relative to 1 mol of hydrogen iodide. Representatively, in the process, in the liquid object, the concentration of acetic acid may be about 0.5 to 50% by weight (e.g., about 0.5 to 40% by weight), the concentration of hydrogen iodide may be about 5 to 1000 ppm (e.g., about 5 to 200 ppm), the ratio of the methanol source (in terms of methanol) may be about 1 to 20 mol (e.g., about 1 to 5 mol) relative to 1 mol of a total amount of acetic acid and hydrogen iodide.

In the process of the present invention, the concentration of the methanol source in the liquid object may be adjusted with the reaction condition or the feed amount beforehand. The concentration of the methanol source in the liquid object is usually adjusted by adding or mixing the methanol source and/or methyl acetate to the overhead (3A) inside or outside the acetaldehyde distillation column (for example, the concentration of the methanol source in the liquid object is adjusted to 0.1 to 50% by weight). Incidentally, although methyl acetate is not a methanol source, methyl acetate can produce methanol by chemical equilibrium. Thus the concentration of the methanol source in the liquid object may be adjusted by addition of methyl acetate. Representatively, the concentration of the methanol source in the liquid object may be adjusted by adding or mixing the methanol source and/or methyl acetate in the following manner (A) and/or manner (B):

(A) the methanol source and/or methyl acetate is added to or mixed with the overhead (3A) before the overhead (3A) is fed to the acetaldehyde distillation column [that is, the methanol source and/or methyl acetate is added to or mixed with the overhead (3A) prior to feeding to the acetaldehyde distillation column], (B) in the acetaldehyde distillation column, the methanol source and/or methyl acetate is added to or mixed with the overhead (3A) at the same height level (or the same position, for example, in the distillation column, the same plate) as a height level (or a position or a plate) at which the overhead (3A) is fed or at a height level (e.g., in the distillation column, a plate) upper than the height level (e.g., in the distillation column, a plate) at which the overhead (3A) is fed.

In the manner (A), a temperature of a mixture containing the overhead (3A) and the methanol source and/or methyl acetate may be regulated to 20 to 100° C., and a time from when the overhead (3A) and the methanol source and/or methyl acetate are mixed till when the mixture is fed to the acetaldehyde distillation column may be regulated to not less than 5 seconds; and the concentration of the methanol source may be adjusted in at least the manner (A). Representatively, in the manner (A), a temperature of a mixture containing the overhead (3A) and the methanol source and/or methyl acetate may be regulated to 30 to 85° C., and a time from when the overhead (3A) and the methanol source and/or methyl acetate are mixed till when the mixture is fed to the acetaldehyde distillation column may be regulated to not less than 10 seconds; and the concentration of the methanol source may be adjusted in at least the manner (A). Feeding of the acetaldehyde distillation column with the overhead (3A) to which the methanol source and/or methyl acetate is added under such a condition can further efficiently inhibit the increase in concentration hydrogen iodide or acetic acid in the acetaldehyde distillation column.

According to the process of the present invention, the overhead (3A) may directly be fed to the acetaldehyde separation step (or acetaldehyde distillation column), and the overhead (3A) may usually be held (or retained) in a decanter and then discharged to be fed to the acetaldehyde separation step. That is, the process of the present invention may further comprise a condensation step for temporarily holding the overhead (3A) in a decanter (or storage vessel) with condensation, and discharging the overhead (3A) from the decanter. The overhead (3A) discharged from the decanter in the condensation step may be fed to the acetaldehyde distillation column. When the process comprises the condensation step, in the manner (A) the methanol source is usually added to or mixed with the overhead (3A) at a time from when the overhead (3A) is discharged from the decanter till when the overhead (3A) is fed to the acetaldehyde distillation column.

In the condensation step, the amount to be held of the overhead (3A) may be adjusted or controlled based on a fluctuating (or changing or varying) flow rate of the overhead (3A) to be fed to the decanter. That is, according to the production process of acetic acid, the amount of the overhead (3A) to be fed to the decanter significantly fluctuates throughout the whole process. Such the control of the flow rate allows the process to be performed stably and efficiently. Thus combination of such a process with the adjustment of the concentration of the methanol source efficiently ensures both the stable operation of the process and the inhibition of an increase in concentration of hydrogen iodide or acetic acid in the acetaldehyde distillation column. With respect to the fluctuation (or change or variation), for example, assuming that the average flow rate of the lower boiling point component (3A) to be fed to the decanter is 100 in terms of liquid volume, the flow rate of the lower boiling point component (3A) to be fed to the decanter may be about 80 to 120 throughout the whole process.

A concrete method for adjusting (or controlling) the amount of the overhead (3A) to be held includes, for example, (1) a method in which the overhead (3A) is discharged so that the fluctuation of the amount or liquid level of the overhead (3A) to be held in the decanter may be inhibited (or substantially kept constant) and/or (2) a method in which a decanter having a buffering function is used as the decanter to ease (or diffuse) the fluctuation of the amount of the overhead (3A) fed inside the decanter.

According to the method (1), for example, in the condensation step, assuming that the average liquid level (or average amount) and/or interface level of the overhead (3A) held in the decanter are/is 100, the liquid level (or average amount) and/or interface level of the overhead (3A) held in the decanter may be adjusted (specifically, the overhead (3A) may be discharged to adjust the liquid level) to about 95 to 105 throughout the whole process. The liquid level means a height level of the contact surface of the condensed overhead (3A) with gas (gas phase) in the decanter. When the overhead (3A) is separated into two phases (upper phase and lower phase), the interface level means a height level of the boundary between two phases (or a height level of the lower phase). Thus the concept of the interface level is used for layer-separated (phase-separated) condensed overhead (3A).

Moreover, according to the adjustment method (2), in the condensation step, a decanter having a buffering function may be used as the decanter. In particular, the retention time (or holding time) of the overhead (3A) in such a decanter may be regulated so as to be not less than 6 minutes. Use of the decanter which allows such a sufficient retention time can efficiently ease the fluctuation of the overhead (3A) in the decanter.

According to the present invention, in order to carry out the whole process stably, in the condensation step the amount of the overhead (3A) to be held may usually be adjusted or controlled based on the fluctuation of the flow rate of the overhead (3A) to be fed to the decanter, and further the amount of the overhead (3A) to be fed to the acetaldehyde separation step may be adjusted. Specifically, in the condensation step, the amount of the overhead (3A) to be fed to the acetaldehyde separation step may be adjusted so as to be constant or almost constant (or substantially be kept constant) [for example, assuming that the average flow rate of the overhead (3A) is 100, the flow rate of the overhead (3A) to be fed to the acetaldehyde separation step may be adjusted to 95 to 105 throughout the whole process].

Representative examples of the method for adjusting or controlling the amount of the overhead (3A) to be fed to the acetaldehyde separation step (or acetaldehyde distillation column) include at least one selected from the following methods (a), (b), and (c): (a) a method for circulating part of the overhead (3A) discharged from the decanter to a step different from the acetaldehyde separation step [for example, at least one selected from the group consisting of the reaction system (reactor or reaction step) and the acetic acid collection step (or distillation column), particularly at least the reaction system (or reactor) or reaction step]; (b) a method for feeding the acetaldehyde separation step with the overhead (3A) discharged from the decanter through a storage vessel having a buffering function; and (c) a method for adjusting the amount of the overhead (3A) to be discharged from the decanter to keep constant (or almost constant, for example, assuming that the average flow rate of the overhead (3A) to be discharged from the decanter is 100, the amount of the lower boiling point component (3A) to be discharged from the decanter throughout the whole process is adjusted to 95 to 105).

For the method (a), in the condensation step, the amount (or flow rate) of the overhead (3A) to be fed to the acetaldehyde separation step may be adjusted by circulating part of the overhead (3A) discharged from the decanter to a step different from the acetaldehyde separation step. In the method (a), not less than 20% (for example, about 20 to 90%) of the average flow rate of the overhead (3A) to be fed to the decanter may be circulated, in particular, about 40 to 90% of the average flow rate may be circulated. Moreover, in the method (a), the overhead (3A) may be separated into an upper layer and a lower layer in the decanter, and the upper layer and the lower layer may be circulated.

For the method (b), the retention time of the overhead (3A) in the storage vessel having a buffering function may be not less than 1 minute (for example, not less than 2 minutes). Moreover, in the method (b), the total time of the retention time of the overhead (3A) in the decanter and the retention time of the overhead (3A) in the storage vessel having a buffering function may be not less than 3 minutes (for example, not less than 4 minutes).

For the method (c), typically, a decanter having a buffering function is used as the decanter, and the retention time of the overhead (3A) in the decanter may be not less than 3 minutes.

The methods (a) to (c) may be carried out alone or in combination (for example, at least the method (a) or the method (b)).

According to the present invention, not only removal of acetaldehyde but also collection (recycling) of methyl iodide is efficiently achieved. For example, the present invention may further comprise a recycling step for feeding the acetaldehyde distillation column with the overhead (3A), separating a lower boiling point component (4A) containing acetaldehyde and a higher boiling point component (4B) containing methyl iodide by distillation, to recycle the higher boiling point component (4B) as a separated solution (or a solution) [for example, to recycle the component to a step from the reaction system (or reactor or reaction step) to the acetaldehyde separation (for example, at least one member selected from the group consisting of the reaction system (reactor or reaction step), the acetic acid collection step (or distillation column), and the acetaldehyde removal column; particularly at least the reactor or reaction step)].

Moreover, according to the present invention, in the recycling step, the separated solution may be recycled while reducing the fluctuation of the flow rate of the separated solution. Specifically, in the recycling step, the separated solution may be recycled through a storage vessel having a buffering function.

The lower boiling point component (4A) sometimes contains methyl iodide due to insufficient separation. Thus, according to the present invention, when the lower boiling point component (4A) contains methyl iodide, in the recycling step methyl iodide collected from the lower boiling point component (4A) may be recycled [recycled to a step from the reaction system to the acetaldehyde separation, for example, recycled to at least one member selected from the group consisting of the reaction system (reactor or reaction step), the acetic acid collection step (or distillation column), and the acetaldehyde distillation column].

In the process of the present invention, the material of (or for forming) the acetaldehyde distillation column may comprise an alloy [for example, a nickel-based alloy, an iron-based alloy (e.g., a stainless steel and a two-phase iron-based alloy (such as a two-phase stainless steel))]. The present invention achieves the inhibition of the corrosion, and even an acetaldehyde distillation column made of such a relatively corrosive material can preferably be used.

Incidentally, throughout this description, the term "liquid object to be treated" (or "liquid object") means a process solution before distilled in the acetaldehyde distillation column unless otherwise noted. Throughout the description, the total of the proportion(s) of any component(s) existing in the same mixture system (such as the liquid object to be treated) is not more than 100% by weight; and the proportions of the all components is 100% by weight in total.

Effects of the Invention

According to the process of the present invention, acetic acid can be produced while efficiently inhibiting (or preventing) an increase in concentration of hydrogen iodide (in particular, hydrogen iodide and acetic acid) in the acetaldehyde distillation column. Moreover, according to the process of the present invention, corrosion of the acetaldehyde distillation column can be inhibited (or prevented). Further, according to the process of the present invention, acetaldehyde can efficiently be removed even if the acetaldehyde distillation column is not made of a high-quality material having a high corrosion resistance. Therefore, according to the process of the present invention, acetaldehyde can efficiently be separated even using an acetaldehyde distillation column made of an inexpensive or low-grade material. Thus the present invention allows use of an inexpensive or low-grade material for making the acetaldehyde distillation column, so that the cost of the production process of acetic acid can efficiently be reduced.

Moreover, according to the present invention, acetic acid (acetic acid with a high purity) can stably be produced while inhibiting an increase in concentration of hydrogen iodide or acetic acid in the acetaldehyde distillation column by adjusting the amount of the overhead to be stored in the decanter in response to the fluctuation of the feed amount of the overhead containing methyl iodide and acetaldehyde as well as while efficiently removing acetaldehyde.

Further, according to the present invention, since acetaldehyde can be separated from the overhead efficiently and reliably, acetic acid can be produced while highly efficiently recycling the catalyst methyl iodide separated from the overhead.

DESCRIPTION OF EMBODIMENTS

Figure 1:
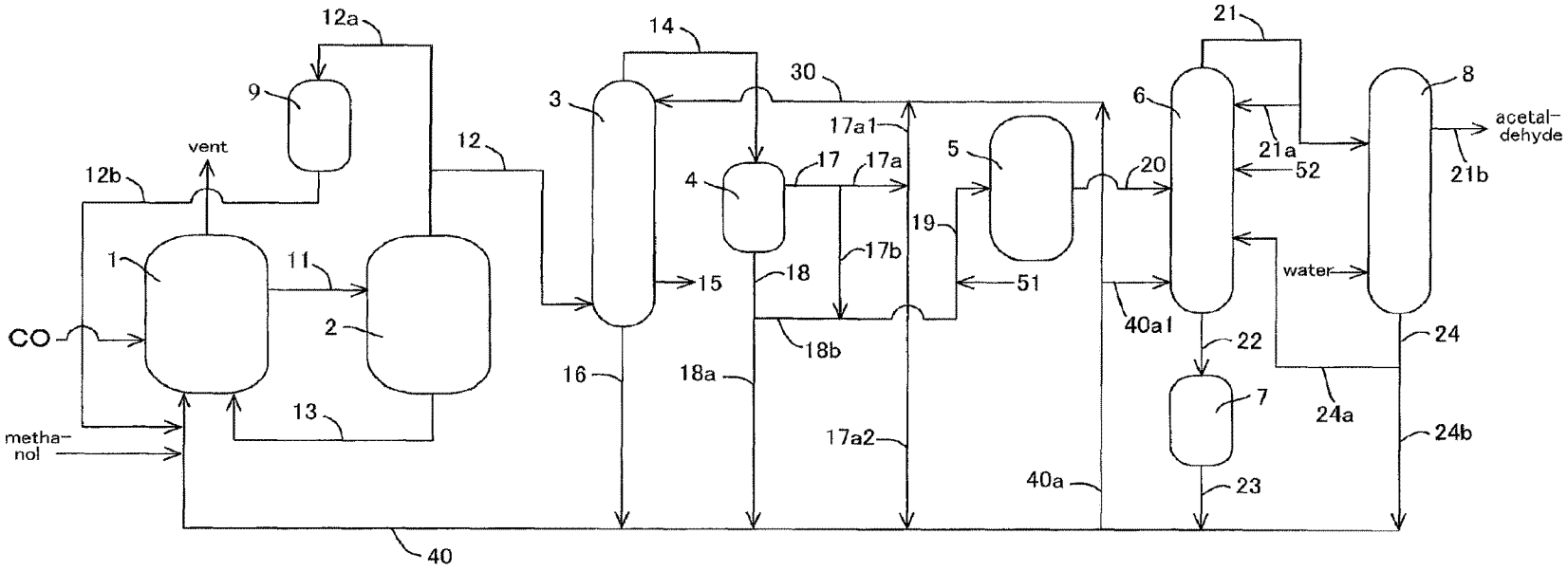
FIG. 1 is a diagram for explaining a production process (or production apparatus) of acetic acid in accordance with an embodiment of the present invention.

Hereinafter, the present invention will be explained in detail with reference to the drawings. FIG. 1 is a diagram (a flow sheet, a schematic process drawing, or a schematic plant layout drawing) for explaining a production process (or production apparatus) of acetic acid in accordance with an embodiment of the present invention.

The embodiment of FIG. 1 shows a continuous process (or apparatus) for producing acetic acid from a liquid reaction medium (or reaction mixture) generated by a continuous carbonylation reaction of methanol with carbon monoxide in the presence of a catalyst system comprising a rhodium catalyst as a metal catalyst and a co-catalyst [lithium iodide as a halide salt and methyl iodide], as well as acetic acid, methyl acetate, and a finite amount of water.

The process (or production apparatus) comprises a reactor (reaction system) 1 for carrying out the carbonylation reaction of methanol; a flasher 2 for separating a volatile component or volatile phase (2A) containing product acetic acid, methyl iodide, methyl acetate, and water and a low-volatile component or low-volatile phase (2B) containing the rhodium catalyst and lithium iodide from a liquid reaction medium (or a reaction mixture or a reaction solution) which contains acetic acid generated by the reaction; a splitter column 3 for separating an overhead (a first overhead) (3A) containing methyl iodide, acetic acid, methyl acetate, water, by-product acetaldehyde, hydrogen iodide, and others, a stream or acetic acid phase (3B) containing acetic acid as a side stream, and a higher boiling point stream or higher boiling point component (3C) containing acetic acid, water, propionic acid, and others, from the volatile component (2A) fed to the flasher 2; a decanter 4 for temporarily holding or storing the condensed overhead (3A); a buffer tank 5 for temporarily storing (or retaining) the overhead (3A) fed or discharged from the decanter 4; an acetaldehyde distillation column (separation column or removal column) 6 for separating the overhead (3A) fed or discharged from the decanter 4 or the buffer tank 5 into a lower boiling point component (4A) containing acetaldehyde and methyl iodide and a higher boiling point component (4B) containing methyl iodide, methyl acetate, water, acetic acid, and others; a buffer tank 7 for temporarily storing (or retaining) the higher boiling point component (4B) separated in the distillation column 6; an extraction apparatus or extractor 8 for separating acetaldehyde from the lower boiling point component (4A) by extraction to recycle methyl iodide; lines 51 and 52 for feeding methanol and/or dimethyl ether; various lines for feeding or circulating each component to these apparatus.

Hereinafter, the process shown in FIG. 1 will be explained in more detail.

To the reactor 1, methanol as a liquid component is continuously fed at a predetermined rate, and carbon monoxide as a gaseous reactant is continuously fed. Moreover, to the reactor 1, a catalyst mixture (liquid catalyst mixture) containing a carbonylation catalyst system [a catalyst system comprising a main metal catalyst component (e.g., a rhodium catalyst) and a co-catalyst (e.g., lithium iodide and methyl iodide)] and water may be fed. Further, a stream (e.g., in the form of liquid) containing lower boiling point component(s) or higher boiling point component(s) from the succeeding step(s) is fed to the reactor 1 through a line 13 and/or a line 40.

Then, inside the reactor 1, a liquid-phase reaction system containing the reactant and the higher boiling point component such as the metal catalyst component (e.g., a rhodium catalyst and lithium iodide) is in equilibrium with a vapor-phase system comprising carbon monoxide, by-products by the reaction (hydrogen, methane, carbon dioxide), and a vaporized lower boiling point component (e.g., methyl iodide, acetic acid as a product, and methyl acetate), and a carbonylation reaction of methanol proceeds. In order to keep the inner pressure of the reactor 1 (e.g., reaction pressure, carbon monoxide partial pressure, hydrogen partial pressure, methane partial pressure, and nitrogen partial pressure) constant, a vapor may be withdrawn and discharged from the top of the reactor 1. Further, the vapor withdrawn from the reactor 1 may be cooled by a heat exchanger to give a liquid component (containing acetic acid, methyl acetate, methyl iodide, acetaldehyde, water, and others) and a gaseous component (containing carbon monoxide, hydrogen, and others). The resulting liquid component may be recycled to the reactor 1 (not shown), and the resulting gaseous component (waste gas) may be discharged.

To the reactor 1, if necessary, hydrogen may be fed in order to increase the catalytic activity. Hydrogen may be fed together with carbon monoxide or may be fed separately. Moreover, since the reaction system is an exothermic reaction system that accompanies heat generation, the reactor 1 may be equipped with a heat-removable (or heat-removing) unit or a cooling unit (e.g., a jacket) for controlling a reaction temperature.

Components contained in the reaction mixture (crude reaction solution) generated in the reactor 1 may include acetic acid, a lower boiling point component or lower boiling point impurity having a boiling point lower than that of acetic acid (e.g., methyl iodide as a co-catalyst, methyl acetate as a reaction product of acetic acid with methanol, water, and acetaldehyde, a higher iodide (such as hexyl iodide) as by-products), and a higher boiling point component or higher boiling point impurity having a boiling point higher than that of acetic acid [e.g., a metal catalyst component (e.g., a rhodium catalyst), lithium iodide as a co-catalyst, propionic acid, and water].

In order to mainly separate the higher boiling point component (such as the metal catalyst component) from the reaction mixture, part of the reaction mixture is continuously withdrawn from the reactor 1 and introduced or fed into the flasher (distillation column or catalyst separation column) 2 through a feed line 11.

The amount of the reaction mixture to be fed from the reactor 1 to the flasher 2 is not constant and fluctuates (or varies) in the continuous process due to the pressure fluctuation caused by sparging of carbon monoxide to be fed to the liquid phase and others. For example, assuming that the average flow rate of the reaction mixture to be fed to the flasher 2 is 100, the flow rate (or flow velocity, hereinafter, the same applies in the flow rate) of the reaction mixture to be fed to the flasher 2 is about 98 to 102 throughout the whole process. As described later, for a closed process, the fluctuation of the feed amount affects the succeeding step(s) and can sometimes be a factor that causes a fluctuation of the feed amount of the overhead to be fed to the decanter.

In the flasher (flash distillation column) 2, from the reaction mixture, a low-volatile component (2B) (mainly containing the metal catalyst component such as the rhodium catalyst or lithium iodide, and others) and a lower boiling point stream or volatile component (2A) (mainly containing acetic acid which is a product and also functions as a reaction solvent, methyl acetate, methyl iodide, water, acetaldehyde, and others) are separated, and the low-volatile component (2B) is withdrawn from the bottom of the flasher through a bottom line 13 and recycled to the reactor 1, and the volatile component (2A) (acetic acid stream) is withdrawn from the column top or upper part of the flasher 2 through a feed line 12 and fed or introduced to the splitter column (or distillation column) 3. Incidentally, the low-volatile component (2B) also contains the metal catalyst (the rhodium catalyst) and the halide salt (lithium iodide), and in addition components remaining without evaporation (e.g., methyl iodide, methyl acetate, water, and a trace of acetic acid). The volume proportion of the volatile component (2A) to be separated in the flasher 2 is about 20 to 40% in the whole reaction mixture.

Part of the lower boiling point component (2A) may be heat-removed and recycled to the reactor. In an embodiment of FIG. 1, part of the vaporized lower boiling point component (2A) (for example, about 10 to 30% by volume) is fed to a storage vessel (hold tank) and/or heat exchanger 9 through a line 12a and condensed by heat removal, and recycled to the reactor 1 through a line 12b. In this manner, heat-removal of part of the lower boiling point component (2A) and circulation of the component to the reactor allows an apparatus such as a distillation column (e.g., a splitter column) to be downsized (or miniaturized) even for a large-sized plant. Thus acetic acid can be produced with a high purity and a high yield in a resource-saving and energy-saving equipment.

The amount (feed amount) of the volatile component (2A) to be fed from the flasher 2 to the splitter column 3 also fluctuates in the continuous process with the fluctuation of the amount (feed amount) of the reaction mixture to be fed to the flasher 2. For example, assuming that the average flow rate of volatile component (2A) to be fed to the splitter column 3 is 100, the flow rate of the volatile component (2A) to be fed to the splitter column 3 is about 98 to 102 throughout the whole process.

In the splitter column 3, usually, an overhead (or lower boiling point component) (3A) (containing methyl iodide, methyl acetate, acetaldehyde, water, acetic acid, hydrogen iodide, and others) is separated from the column top or upper part of the column through a withdrawing line 14, and a higher boiling point stream or higher boiling point component (3C) (a component containing water, propionic acid, and others) is separated (or removed) from the bottom or lower part of the column through a bottom line 16. The separated higher boiling point component (3C) may be discharged through a line 16, or may partly or wholly be recycled to the reactor 1 through a line 40. A side stream or acetic acid phase stream (3B) (acetic acid stream) mainly containing acetic acid is collected from the splitter column 3 through a feed line 15 by side cut. Incidentally, the stream (3B) containing acetic acid collected by side cut may usually be fed to another distillation column (not shown) through the line 15 and then distilled for purification (not shown). The proportion of the overhead (3A) separated in the splitter column 3 is about 35 to 50% by weight in the whole volatile component (2A). As described later, when a process solution from the succeeding steps) is circulated or recycled to the splitter column 3, the total amount of the component to be fed from the flasher 2 and the component recycled from the succeeding step(s) is subjected to distillation in the splitter column 3 to separate the overhead (3A).

The amount of the overhead (3A) to be fed from the splitter column 3 to the decanter 4 is affected by the fluctuation of the amount of the reaction mixture to be fed to the flasher 2 and the fluctuation of the amount of the volatile component (2A) to be fed from the flasher 2 to the splitter column 3, and fluctuates in the continuous process. For example, assuming that the average flow rate of the overhead (3A) to be fed to the decanter 4 is 100, the flow rate of the overhead (3A) to be fed to the decanter 4 is about 90 to 110 throughout the whole process (that is, the flow rate of the overhead (3A) fluctuates within the range of about 0 to ±10% by volume). The overhead (3A) is fed to the decanter 4 with such a relatively large fluctuation.

The overhead (3A) separated through the line 14 is condensed, continuously fed to the decanter (storage vessel) 4, and temporarily held (stored) in the decanter 4. Inside the decanter 4, the condensed overhead (3A) is separated into an upper layer and a lower layer; the upper layer (water layer or aqueous phase) mainly contains water, acetic acid, methyl acetate, and others and the lower layer (organic layer or organic phase) mainly contains methyl iodide, methyl acetate, and others. Acetaldehyde, methyl iodide, and hydrogen iodide are contained in the both layers. A larger quantity of acetaldehyde is contained in the upper layer (water layer) compared to the lower layer. Hydrogen iodide is mainly contained in the upper layer in many cases. In the overhead (3A) to be fed to the decanter 4, the volume ratio of the upper layer (or upper layer component) relative to the lower layer (or lower layer component) [the former/the latter] is, for example, about 0.5/1 to 1.5/1 (e.g., about 0.7/1 to 1.3/1). The fluctuation of the feed amount in the upper layer and the lower layer is within the same range as that mentioned above.

The overhead (3A) held in the decanter 4 is fed to the acetaldehyde distillation column 6 through a feed line 17 and/or a feed line 18. In the embodiment of FIG. 1, the storage of the overhead (3A) to be held in the decanter 4 (or the fluctuation of the liquid level) is significantly restrained from fluctuating by circulating (or recycling) part of the overhead (3A) to the reaction system or others through a line 17a (sub-line 17a) branched from the line 17 or a line 18a (sub-line 18a) branched from the line 18 based on the flow rate fluctuation of the overhead (3A) to be fed to the decanter 4.

That is, the amount of the overhead (3A) to be continuously fed to the decanter 4 (for example, the amount to be fed per unit of time) is not constant in the continuous reaction, and as described above, the amount fluctuates through the carbonylation reaction, the flash distillation, and the recycling of the methyl iodide (for example, the amount of the overhead (3A) to be fed per unit of time is increased or decreased). Accordingly, direct feeding of the overhead (3A) to the decanter 4 causes large fluctuation of the liquid level of the overhead (3A) condensed and stored in the decanter 4, and, sometimes the process cannot be operated depending on the fluctuation. In order to ease (or reduce) the fluctuation, the overhead (3A) may be fed from the decanter 4 to the acetaldehyde distillation column 6 at a flow rate enough to ease the fluctuation of the flow rate. However, such feeding causes insufficient process in the aldehyde distillation column 6.

Then, in the embodiment of FIG. 1, the amount of the overhead (3A) to be held in the decanter 4 is adjusted or controlled by recycling part of the overhead (3A) to a step (in the embodiment of FIG. 1, the reactor 1 and/or the splitter column 3) different from the acetaldehyde separation step without feeding from the decanter 4 to the distillation column 6 based on the fluctuation of the flow rate of the overhead (3A) to be fed to the decanter 4.

Specifically, in the embodiment of FIG. 1, the overhead (3A) is discharged from the upper layer and the lower layer in the decanter 4 through the line 17 and the line 18, respectively. The flow rate of the overhead (3A) to be discharged from the decanter 4 is regulated so that each of the liquid levels of the upper layer and the lower layer may be constant (or almost constant) even under the fluctuation of the flow rate overhead (3A) to be fed to the decanter 4. That is, the decanter 4 is provided with liquid level sensors for detecting liquid level fluctuation (not shown), and one of the sensors detects the liquid level fluctuation of the upper layer and the other detects that of the lower layer. The amount of the overhead (3A) to be discharged from the upper layer and the lower layer in the decanter 4 is regulated based on the liquid level information detected by the sensors so that predetermined liquid levels of these layers may be maintained. More specifically, based on the information obtained by the liquid level sensors, when the flow rate to be fed to the decanter is large, the flow rate of the overhead (3A) to be discharged is increased to prevent the liquid level from raising; when the flow rate to be fed to the decanter is small, the flow rate of the overhead (3A) to be discharged is decreased. In such a way, the liquid level (or liquid level of the upper layer) of the overhead (3A) in the decanter 4 (the liquid level of the upper layer and that of the lower layer) is kept constant or almost constant by adjusting (controlling) the flow rate throughout the whole process [for instance, assuming that the average liquid level is 100, each of the liquid level of the upper layer and that of the lower layer is regulated (or adjusted) to about 99 to 101 throughout the whole process, that is, the liquid level fluctuation is adjusted to at most about 1% in the whole process].

Further, a portion of the overhead (3A) discharged through the line 17 and the line 18 is fed to a line 19 through the line 17b and line 18b. The flow rate of the overhead (3A) to be fed to the line 19 is adjusted (controlled) to keep constant or almost constant by adjusting the amount of the overhead (3A) to be circulated through the line 17a and/or the line 18a. That is, in the embodiment of FIG. 1, as described above, the amount of the overhead (3A) discharged from each of the upper layer and the lower layer in the decanter 4 fluctuates so that the liquid level in the decanter 4 may be constant or almost constant. By changing the amount of the overhead (3A) to be circulated through the line 17a and/or the line 18a in response to the fluctuation, the flow rate of the overhead (3A) to be fed to the line 19 is regulated to be avoid (or almost avoid) from fluctuating [for instance, assuming that the average flow rate of the overhead (3A) to be fed to the line 19 is 100 in terms of liquid volume, the flow rate of the overhead (3A) is regulated (or adjusted) to about 98 to 102 throughout the whole process, that is, the fluctuation of the flow rate is adjusted to at most about 2% in the whole process]. Incidentally, in the embodiment of FIG. 1, the flow rate fluctuation of the lower boiling point component (3A) to be fed to the line 19 can mainly be controlled by fluctuating the amount of the overhead (3A) to be circulated, and additionally can further be controlled by regulating the retention time of the overhead (3A) in the decanter 4.

It is sufficient that the flow rate of the overhead (3A) to be fed to the line 19 is regulated by fluctuating the flow rate of the overhead (3A) to be circulated to the line 17a and/or the line 18a. As far as large fluctuation of the flow rate to be fed to the line 19 is not caused, the flow rate of the overhead (3A) to be circulated to the line 17a or the line 18a may be kept constant (in other words, the flow rate of the overhead (3A) to be fed to the line 17b or the line 18b may fluctuate).

Moreover, in the embodiment of FIG. 1, the overhead (3A) is discharged through the line 17 and the line 18. The flow rate of the overhead (3A) to be fed to the line 19 may be regulated by discharging the overhead (3A) through only one of the lines 17 and 18 and circulating part of the overhead (3A). Further, without reference to the upper layer and the lower layer, the overhead (3A) may be fed or discharged through a single line.

The overhead (3A) to be fed to the line 17a may be fed to a line 30 through a line 17a1 and circulated to the splitter column 3, may be fed to a line 40 through a line 17a2 and recycled (or returned) to the reactor 1, or may be recycled through both lines 17a1 and 17a2. Moreover, the overhead (3A) to be fed to the line 18a is fed to the line 40 and recycled to the reactor 1.

Since the fluctuation of the flow rate of the overhead (3A) to be fed to the line 19 is significantly inhibited as described above, the overhead (3A) may directly be fed to the distillation column 6. In the embodiment of FIG. 1, in order to further ease (or reduce) the fluctuation of the flow rate, the overhead (3A) is fed to the distillation column 6 through a storage vessel (buffer tank) 5 having a buffering function. That is, the overhead (3A) fed to the line 19 is fed to the buffer tank 5 and then fed to the distillation column 6 through a line 20. By temporarily retaining the overhead (3A) in the buffer tank 5 in such a way, even when the amount to be fed from the buffer tank 5 to the line 20 is kept constant (or almost constant), the fluctuation of the flow rate of the overhead (3A) fed from the line 19 in the buffer tank 5 can efficiently be eased (or reduced).

To the overhead (3A) to be subjected to distillation in the distillation column 6, a predetermined quantity of a methanol source (methanol and/or dimethyl ether) is added or mixed through a line 51 and/or a line 52. That is, the predetermined quantity of the methanol source (methanol and/or dimethyl ether) may be added or mixed in the line 19 through the line 51. Specifically, the overhead (3A), which contains acetic acid, methyl acetate, water, and hydrogen iodide in addition to methyl iodide and acetaldehyde, is fed in the form of a mixture (liquid object to be treated, process solution) containing the methanol source to the buffer tank 5 and then the distillation column 6 through the line 20. In the embodiment of FIG. 1, the methanol source is added in the line 19 before feeding to the buffer tank 5. The methanol source may be added in the line 20 through the line 51 just before feeding to the distillation column 6.

Moreover, the methanol source is fed through the line 52 at the same plate (or height level or position) as a plate (or height level or position) at which the overhead (3A) is fed to the distillation column 6 through the line 20 or at an upper plate (or height level or position) relative to that plate (or height level or position); and a mixture containing the methanol source and the overhead (3A) can be subjected to distillation. Feeding of the methanol source to the distillation column 6 at such a relative position can also reliably inhibit the increase in concentration of hydrogen iodide (and acetic acid) at the plate (or height level or position) feeding the overhead (3A) or an upper plate (or height level or position) thereof. Thus the corrosion of the whole distillation column 6 can also be inhibited efficiently.

To the line 51 and/or the line 52, methyl acetate may be added instead of the methanol source or added together with the methanol source.

Considering the concentration of the methanol source in the distillation column 6, the amount of the methanol source (and/or methyl acetate; the same applies in others) to be added in each of the line 51 and/or the line 52 may be regulated so that the methanol source may have a predetermined concentration at an appropriate proportion.

The mixture, containing the overhead (3A), fed to the distillation column 6 is separated into a lower boiling point stream or lower boiling point component (or a second overhead) (4A) and a higher boiling point stream or higher boiling point component (4B) in the distillation column 6 by distillation; wherein the lower boiling point stream (4A) contains a trace of methyl iodide, carbon monoxide, hydrogen, and others in addition to acetaldehyde, and the higher boiling point stream (4B) contains methyl acetate, water, and others in addition to methyl iodide. The increase in concentrations of hydrogen iodide and acetic acid in the distillation column 6 is significantly inhibited by the distillation of the overhead (3A) together with the methanol source. Due to the addition of dimethyl ether, the increase in hydrogen iodide concentration seems to be inhibited in association with a plurality of reactions including the following reaction.

$$CH_3OCH_3+2HI \Leftrightarrow 2CH_3I+H_2O$$

The separated lower boiling point component (4A) is fed from the column top or upper part to an acetaldehyde extraction apparatus (water extraction column) 8 through a line (discharge line) 21, and acetaldehyde is extracted from the lower boiling point component (4A) using water. The extracted acetaldehyde (aldehyde aqueous solution) is discharged through a line 21b. Incidentally, part of the lower boiling point component (4A) may be returned to the distillation column 6 through a line 21a. Moreover, the raffinate containing a trace of methyl iodide, and others may be discharged out of the system. In the embodiment of FIG. 1, the raffinate discharged through a line 24 is fed to the distillation column 6 through a line 24a, and/or is fed to a line 40 through a line 24b to be recycled to the reactor 1. In such a manner, the distillation or recycling of the raffinate can further improve a recovery percentage of methyl iodide.

Moreover, the separated higher boiling point component (4B) is fed as a separated solution (bottom fraction or column bottom fraction) through a line 22 to a line 40, leading to the reactor 1 or the splitter column 3. In such a manner, the useful component containing methyl iodide is circulated (recycled) to the reaction system and others. The higher boiling point component (4B) may directly be fed to the line 40 through the line 22. In the embodiment of FIG. 1, the higher boiling point component (4B) is fed to the buffer tank 7 and then to the line 40 through a line 23. That is, although the fluctuation of the flow rate of the higher boiling point component (4B) to be fed through the line 22 is inhibited with the highly controlled flow rate of the overhead (3A) to be fed to the distillation column 6 as described above, recycling of the raffinate after the acetaldehyde extraction mentioned above, and other factors sometimes cause the flow rate fluctuation of the higher boiling point component (4B). However, even if the flow rate of the higher boiling point component (4B) fluctuates, temporary retention of the higher boiling point component (4B) to be fed through the line 22 in the buffer tank 7 allows the fluctuation in the buffer tank 7 to be eased. Thus the higher boiling point component (4B) can be fed to the line 40 while keeping the flow rate of the higher boiling point component (4B) to be fed to the line 23 constant (or almost constant). Therefore, the flow rate fluctuation of the higher boiling point component (4B) to be recycled can be inhibited (or reduced).

The higher boiling point component (4B) fed to the line 40 may partly or wholly be recycled to the splitter column 3 through a line 40a. The higher boiling point component (4B) fed to the line 40a may partly or wholly be fed to the distillation column 6 through a line 40a1 as far as stable operation of the distillation column 6 can be ensured.

Figure 2:
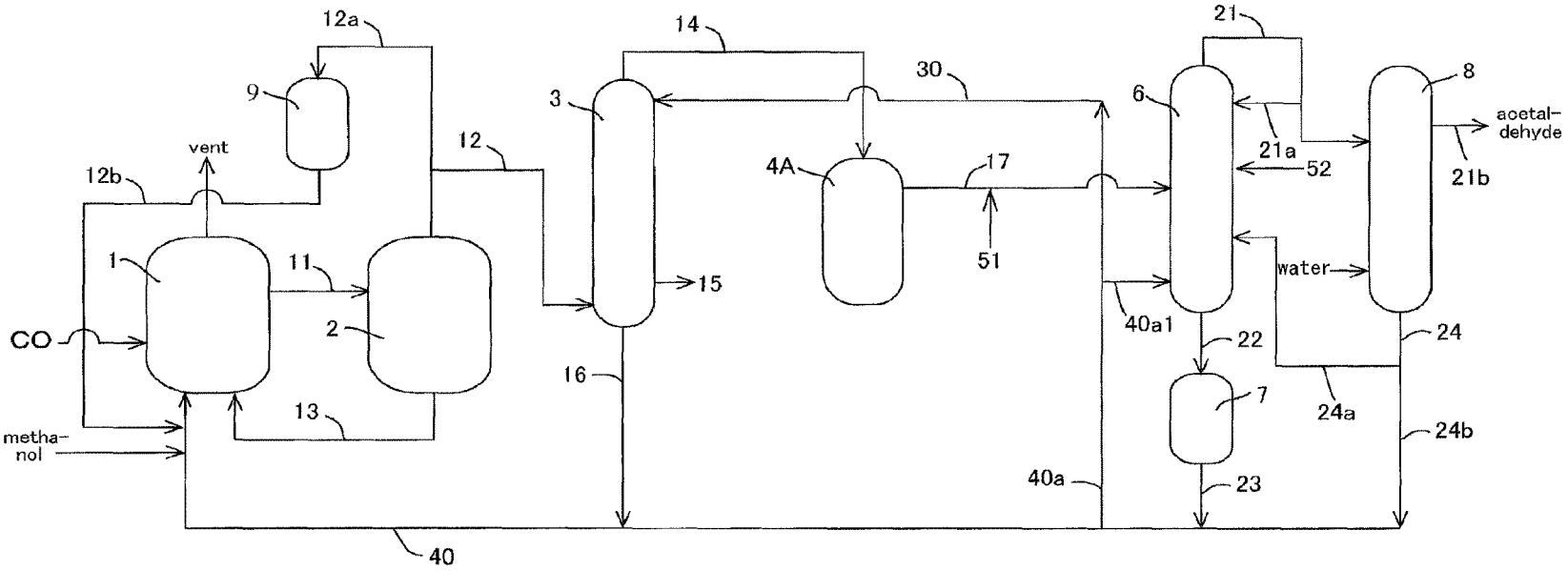
FIG. 2 is a diagram for explaining a production process (or production apparatus) of acetic acid in accordance with another embodiment of the present invention.

FIG. 2 is a diagram for explaining a production process (or production apparatus) of acetic acid in accordance with another embodiment of the present invention. The process (or apparatus) of FIG. 2 is the same as that of FIG. 1 except that a decanter 4A having a buffering function is used instead of the decanter 4 in FIG. 1 and that the overhead (3A) is directly fed to the distillation column 6 through the line 17.

That is, as the embodiment of FIG. 1, usually, the decanter cannot fully ease the flow rate fluctuation of the overhead (3A) to be fed from the splitter column 3. In contrast, in an embodiment of FIG. 2, the decanter 4A having a large capacity enough to ease (reduce) the flow rate fluctuation is used, and the flow rate to be discharged to the line 17 can be kept constant or almost constant by easing the flow rate fluctuation inside the decanter 4A (for instance, assuming that the average flow rate of the overhead (3A) to be fed through the line 14 is 100 in terms of liquid volume, the flow rate of the overhead (3A) to be discharged or fed to the line 17 throughout the whole process can be regulated (or adjusted) to about 98.5 to 101.5, that is, the fluctuation of the flow rate can be adjusted to at most about 1.5%).

In the embodiment of FIG. 2, the overhead (3A) is fed as the upper layer to the distillation column 6 through the line 17. The overhead (3A) may be fed as the lower layer through the line 18 as shown in the embodiment of FIG. 1, or may be fed through both the line 17 and the line 18 (not shown). Further, without reference to the upper layer and the lower layer, the overhead (3A) may be fed through a single line.

(Reaction Step)

In the reaction step (carbonylation reaction step), methanol is carbonylated with carbon monoxide in the presence of the catalyst system. Incidentally, fresh methanol may be fed to the reaction system directly or indirectly, or methanol and/or a derivative thereof withdrawn from various distillation steps may be recycled and fed to the reaction system.

The catalyst system may usually comprise a metal catalyst, a co-catalyst, and an accelerator. Examples of the metal catalyst may include a transition metal catalyst, in particular, a metal catalyst containing the group 8 metal of the Periodic Table (e.g., a cobalt catalyst, a rhodium catalyst, and an iridium catalyst). The catalyst may be a metal as a simple substance or may be used in the form of a metal oxide (including a complex metal oxide), a hydroxide, a halide (e.g., a chloride, a bromide, and an iodide), a carboxylate (e.g., an acetate), a salt of an inorganic acid (e.g., a sulfate, a nitrate, and a phosphate), a complex, and others. These metal catalysts may be used alone or in combination. The preferred metal catalyst includes a rhodium catalyst and an iridium catalyst (particularly, a rhodium catalyst).

Moreover, it is preferred to use the metal catalyst in the form dissolvable in a reaction solution. Incidentally, since rhodium usually exists as a complex in the reaction solution, the form of the rhodium catalyst is not particularly limited to a specific one as long as the catalyst can change into a complex in the reaction solution, and may be used in various forms. As such a rhodium catalyst, a rhodium iodide complex [for example, $RhI_3$, $[RhI_2(CO)_4]^-$, and $[Rh(CO)_2I_2]^-$], a rhodium carbonyl complex, or the like is particularly preferred. Moreover, the catalyst may be stabilized in the reaction solution by addition of a halide salt (e.g., an iodide salt) and/or water.

The concentration of the metal catalyst is, for example, about 10 to 5000 ppm (on the basis of weight, the same applies hereinafter), preferably about 100 to 4000 ppm, more preferably about 200 to 3000 ppm, and particularly about 300 to 2000 ppm (e.g., about 500 to 1500 ppm) in the whole liquid phase in the reactor.

As the co-catalyst or the accelerator contained in the catalyst system, a halide salt (e.g., an iodide salt) is used. The iodide salt is added in order to stabilize the rhodium catalyst and inhibit side reactions, particularly, in a low water content. The iodide salt is not particularly limited to a specific one as far as the iodide salt produces an iodide ion in the reaction solution. The iodide salt may include, for example, a metal halide [for example, a metal iodide such as an alkali metal iodide (e.g., lithium iodide, sodium iodide, potassium iodide, rubidium iodide, and cesium iodide), an alkaline earth metal iodide (e.g., beryllium iodide, magnesium iodide, and calcium iodide), or an iodide of the group 3B metal of the Periodic Table (e.g., boron iodide and aluminum iodide), a bromide corresponding to the iodide, and a chloride corresponding to the iodide], an organic halide [for example, an organic iodide such as a phosphonium salt of an iodide (a phosphonium iodide) (e.g., a salt with tributylphosphine and triphenylphosphine) or an ammonium salt of an iodide (an ammonium iodide) (e.g., a salt of tertiary amine, a pyridine compound, an imidazole compound, an imide compound, or the like with an iodide), a bromide corresponding to the iodide, and a chloride corresponding to the iodide]. Incidentally, the alkali metal iodide (e.g., lithium iodide) also functions as a stabilizer for the carbonylation catalyst (e.g., a rhodium catalyst). These halide salts may be used alone or in combination. Among these halide salts, an alkali metal iodide (such as lithium iodide) is preferred.

In the reaction system (liquid reaction mixture) in the reactor, the concentration of the halide salt (e.g., an iodide salt) is, for example, about 1 to 25% by weight, preferably about 2 to 22% by weight, and more preferably about 3 to 20% by weight in whole liquid phase in the reactor. Further, the concentration of the iodide ion in the reaction system may for example be about 0.07 to 2.5 mol/liter and preferably about 0.25 to 1.5 mol/liter.

As the accelerator contained in the catalyst system, an alkyl iodide (e.g., a $C_{1-4}$alkyl iodide such as methyl iodide, ethyl iodide, or propyl iodide), particularly methyl iodide, is utilized. Since the reaction is promoted at higher concentrations of the accelerator, an economically advantageous concentration can suitably be selected in consideration of the recovery of the accelerator, the plant size of a step for circulating the recovered accelerator to the reactor, the amount of energy necessary for the recovery or circulation, and others. In the reaction system, the concentration of the alkyl iodide (particularly methyl iodide) is, for example, about 1 to 20% by weight, preferably about 5 to 20% by weight, and more preferably about 6 to 16% by weight (e.g., about 8 to 14% by weight) in the whole liquid phase in the reactor.

The reaction is a continuous reaction, and the reaction solution contains methyl acetate. The proportion of methyl acetate may be about 0.1 to 30% by weight, preferably about 0.3 to 20% by weight, and more preferably about 0.5 to 10% by weight (e.g., about 0.5 to 6% by weight) in whole reaction solution.

The carbon monoxide to be fed to the reaction system may be used as a pure gas or may be used as a gas diluted with an inactive gas (e.g., nitrogen, helium, and carbon dioxide). Moreover, exhausted gas component(s) containing carbon monoxide obtained from the succeeding step(s) may be recycled to the reaction system. The carbon monoxide partial pressure in the reactor may for example be about 2 to 30 atmospheres and preferably about 4 to 15 atmospheres.

In the carbonylation reaction, hydrogen is formed (or generated) by a shift reaction between carbon monoxide and water. Hydrogen may be fed to the reaction system. The hydrogen may be fed as a mixed gas with carbon monoxide as a raw material to the reaction system. Moreover, the hydrogen may be fed to the reaction system by recycling gaseous component(s) (including hydrogen, carbon monoxide, and others) exhausted in the succeeding distillation step(s) (distillation column), if necessary after suitably purifying the gaseous component(s). The hydrogen partial pressure in the reaction system may for example be about 0.5 to 250 kPa, preferably about 1 to 200 kPa, and more preferably about 5 to 150 kPa (e.g., about 10 to 100 kPa) in terms of absolute pressure.

The carbon monoxide partial pressure or hydrogen partial pressure in the reaction system may be adjusted, for example, by suitably adjusting the amount of the carbon monoxide and hydrogen fed and/or recycled to the reaction system, the amount of raw substances (e.g., methanol) fed to the reaction system, the reaction temperature, the reaction pressure, and others.

In the carbonylation reaction, the reaction temperature may be, for example, about 150 to 250° C., preferably about 160 to 230° C., and more preferably about 180 to 220° C. Moreover, the reaction pressure (total reactor pressure), including partial pressures of by-products, may be, for example, about 15 to 40 atmospheres.

The reaction may be carried out in the presence or absence of a solvent. The reaction solvent is not limited to a specific one as long as the reactivity, or the separation or purification efficiency does not decrease, and a variety of solvents may be used. In usual cases, acetic acid as a product may be practically utilized as a solvent. That is, in the reaction solution, the remaining main component may be acetic acid, which is a reaction product and serves as a reaction solvent.

The concentration of water in the reaction system is not limited to a specific one, and may be a low concentration. The concentration of water in the reaction system is, for example, not more than 15% by weight (e.g., about 0.1 to 12% by weight), preferably not more than 10% by weight (e.g., about 0.1 to 8% by weight), and more preferably about 0.1 to 5% by weight and may usually be about 1 to 15% by weight (e.g., about 2 to 10% by weight) in the whole liquid-phase of the reaction system. The solubility of carbon monoxide in the solution fed to the flasher is decreased by carrying out the reaction while maintaining a specified concentration of each component [particularly, an iodide salt (lithium iodide) and water] in the reaction system, and the loss of carbon monoxide can be reduced.

In the foregoing carbonylation reaction, production of acetic acid is accompanied by production of an ester of the produced acetic acid with methanol (methyl acetate), water generated with the esterification reaction, additionally acetaldehyde, propionic acid, and others.

Incidentally, since acetaldehyde is separated by the aftermentioned acetaldehyde separation step, the concentration of acetaldehyde in the reactor is held down and is relatively low in spite of the continuous reaction. For example, the concentration of acetaldehyde in the reactor (or reaction system) may be, on the basis of weight, not more than 1000 ppm (e.g., 0 or detection limit to 700 ppm) and preferably not more than 400 ppm (e.g., 5 to 300 ppm) in the liquid phase in the reactor throughout the whole process.

Moreover, inside of the reactor, by-products derived from acetaldehyde is also produced (for example, crotonaldehyde, which is a reducing substance, produced by aldol condensation of acetaldehyde; 2-ethylcrotonaldehyde produced by aldol condensation of hydrogenated crotonaldehyde and acetaldehyde; and hexyl iodide produced through aldol condensation of three acetaldehyde molecules, hydrogenation, and iodization). According to the present invention, since the fluctuation of the concentration of acetaldehyde in the reactor is also inhibited, the combination of the inhibition and the low acetaldehyde concentration mentioned above can significantly decrease by-products derived from acetaldehyde. That is, these by-products are often produced in proportion to the second to third power of the acetaldehyde concentration, and the inhibited (or decreased) acetaldehyde concentration and fluctuation can efficiently induce inhibition of the by-production.

The space time yield of the objective acetic acid in the reaction system may be, for example, about 5 mol/Lh to 50 mol/Lh, preferably about 8 mol/Lh to 40 mol/Lh, and more preferably about 10 mol/Lh to 30 mol/Lh.

The vapor component may be withdrawn from the top of the reactor for the purpose of the pressure control of the reactor or others, and the withdrawn vapor component may be cooled with a condenser, a heat exchanger or other means to remove part of the reaction heat. The cooled vapor component may be separated into a liquid component (containing acetic acid, methyl acetate, methyl iodide, acetaldehyde, water, and others) and a gaseous component (containing carbon monoxide, hydrogen, and others), and the liquid component may be recycled to the reactor.

(Flash Evaporation Step)

In the flash distillation step (flasher), from the reaction mixture fed from the reaction step or the reactor to the flasher (evaporator or flash distillation column), a low-volatile component or low-volatile phase (2B) containing at least a higher boiling point catalyst component (a metal catalyst component, e.g., a rhodium catalyst and a halide salt) is separated as a liquid (component), and a volatile component or volatile phase (2A) containing acetic acid and methyl iodide is separated as a vapor (component).

As described above, the feed amount of the reaction mixture to the flasher fluctuates. With respect to the degree of the fluctuation, assuming that the average flow rate (in terms of liquid volume; the same applies in others unless otherwise noted) of the reaction mixture to be fed to the flasher is 100, the flow rate of the reaction mixture to be fed to the flasher is about 90 to 110 (e.g., about 93 to 107), preferably about 95 to 105 (e.g., about 97 to 103), and more preferably about 98 to 102 (e.g., about 98.5 to 101.5) throughout the whole process.

The separation (flash distillation) of the metal catalyst component may be conducted by a conventional separation method or a conventional separation apparatus, and may usually be carried out with the use of a flash distillation column. Moreover, the metal catalyst component may be separated by means of flash distillation in combination with a mist-collecting method or a solid-collecting method which is widely used in industrial application.

In the flash evaporation step, the reaction mixture may be separated into the vapor component (or vaporized stream) and the liquid component (or liquid stream) with or without heating. For example, in adiabatic flash, the reaction mixture may be separated into the vapor component and the liquid component without heating and with reduced pressure, and in thermostatic flash, the reaction mixture may be separated into the vapor component and the liquid component with heating (and reduced pressure). The reaction mixture may be separated into the vapor component and the liquid component by combining these flash conditions. These flash distillation steps may be carried out, for example, at a temperature of about 80 to 200° C. under a pressure (absolute pressure) of about 50 to 1,000 kPa (e.g., about 100 to 1,000 kPa), preferably about 100 to 500 kPa, and more preferably about 100 to 300 kPa.

The separation step of the liquid catalyst mixture may be composed of a single step, or may be composed of a plurality of steps in combination. The liquid catalyst mixture or higher boiling point catalyst component (metal catalyst component) separated by such step(s) may usually be recycled to the reaction system, as shown in the embodiment of the figure.

Moreover, part of the volatile component (2A) may be recycled to the reactor or the reaction system, as described above. The volatile component (2A) to be recycled may be heat-removed and condensed in a suitable method to be recycled to the reactor. The proportion of the volatile component (2A) to be recycled may for example be about 1 to 50% by volume (e.g., about 5 to 45% by volume), preferably about 10 to 40% by volume, more preferably about 10 to 30% by volume.

The separated volatile component (2A) contains product acetic acid, in addition, hydrogen iodide, a co-catalyst (such as methyl iodide), methyl acetate, water, by-product(s) (e.g., an aldehyde such as acetaldehyde, and propionic acid) and others, and is fed to a distillation column for collecting acetic acid. The proportion of the volatile component (2A) to be fed to the acetic acid collection step in the whole reaction mixture may for example be about 5 to 50% by weight, preferably about 8 to 40% by weight, and more preferably about 10 to 35% by weight (e.g., about 12 to 30% by weight).

(Acetic Acid Collection Step)

In the acetic acid collection step, the volatile component (2A) is fed to the distillation column (splitter column) and separated into an overhead (3A) containing methyl iodide, acetic acid, methyl acetate, by-product acetaldehyde, and hydrogen iodide and a stream (3B) containing acetic acid to collect acetic acid. Specifically, in the distillation column, the overhead (3A) containing methyl iodide, methyl acetate, acetic acid, acetaldehyde, hydrogen iodide, water, and others is separated as a vapor from the volatile component (2A) (acetic acid stream) fed from the flasher; and the liquid stream (3B) (side cut stream, side stream) containing acetic acid is withdrawn. The liquid stream (3B) containing acetic acid may be withdrawn by side cut or withdrawn from the bottom of the distillation column. Incidentally, in the distillation column, a higher boiling point component (3C) containing water, propionic acid, an entrained metal catalyst component, the halide salt, and others may be separated. The higher boiling point component (3C) may be removed (discharged) from the bottom of the distillation column. Since the higher boiling point component (3C) contains a useful component such as the metal catalyst component or acetic acid remaining without being evaporated, and the component (3C) may be recycled to the reactor (or reaction step), the flash evaporation step (or distillation column), or others, as the embodiment of the figure. Incidentally, prior to recycling, propionic acid, which deteriorates the quality of acetic acid as a final product, may be removed off. The acetic acid stream (crude acetic acid solution) is usually dehydrated in the next distillation column and then introduced into an acetic acid purification column for separating higher and lower boiling point components by distillation to give product acetic acid.

Moreover, as described later, the higher boiling point component (3C) to be recycled may be recycled to the reaction system or others through a storage vessel having a buffering function.

As described above, the amount of the lower boiling point component (2A) to be fed to the distillation column is also affected by the fluctuation of the amount fed from the reactor and fluctuates in many cases. With respect to the degree of the fluctuation, for example, assuming that the average flow rate of the volatile component (2A) to be fed to the distillation column is 100, the flow rate of the volatile component (2A) to be fed to the distillation column (2A) is about 90 to 110 (e.g., about 93 to 107), preferably about 95 to 105 (e.g., about 97 to 103), and more preferably about 98 to 102 (e.g., about 98.5 to 101.5) throughout the whole process.

In the distillation column (splitter column), the position of a feed port for feeding the lower boiling point component (2A) is not particularly limited to a specific one. For example, the position of the feed port may be in an upper part, a middle part, or a lower part of the distillation column. Moreover, in the distillation column, the lower boiling point component (2A) may be fed at an upper position or a lower position relative to a side stream port for side-cutting the acetic acid stream. Further, the position of the side stream port for side-cutting the acetic acid stream may be in an upper part, a middle part, or a lower part of the distillation column, and usually, the position of the side stream port is preferably in a middle part or a lower part of the distillation column.

As the distillation column, there may be used a conventional distillation column, for example, a plate column, a packed column, and a flash distillation column. A distillation column such as a plate column or a packed column may be usually employed. Incidentally, the material of (or for forming) the distillation column is not limited to a specific one, and a glass, a metal, a ceramic, or others can be used. In usual, a distillation column made of a metal is used practically.

The distillation temperature and pressure in the distillation column may suitably be selected depending on the condition such as the species of the distillation column, or the main subject (target) for removal selected from the lower boiling point component and the higher boiling point component. For example, in the distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the distillation column, the theoretical number of plates may be about 10 to 80, preferably about 12 to 60, and more preferably about 15 to 40. Further, in the distillation column, the reflux ratio may be selected from, for example, about 0.5 to 3,000, and preferably about 0.8 to 2,000 depending on the above-mentioned theoretical number of plates, or may be reduced by increasing the theoretical number of plates.

The separated overhead (3A) practically contains methyl iodide, acetaldehyde, hydrogen iodide, and in addition acetic acid, methyl acetate, water, and others. The proportion of the overhead (3A) to be fed to the condensation step (or decanter) or the acetaldehyde removal step (or acetaldehyde removal column) may for example be about 5 to 70% by volume, preferably about 10 to 65% by volume, and more preferably about 12 to 60% by volume (e.g., about 15 to 50% by volume) in the whole volatile component (2A).

(Condensation and Discharge Step)

According to the process of the present invention, the overhead (3A) may directly be fed to the acetaldehyde separation step (4) (or acetaldehyde distillation column). The overhead (3A) may usually be condensed and then fed to the acetaldehyde separation step. Typically, the process of the present invention may further comprise a condensation and discharge step for temporarily holding the overhead (3A) in a decanter (or storage vessel) and discharging the overhead (3A) from the decanter (the step may simply be referred to as a condensation step or the like).

In the condensation step, the separated lower boiling point component (3A) is temporarily held (or stored) in the decanter (or storage vessel) while condensing, and then discharged to be subjected to at least the acetaldehyde separation step. In particular, according to the present invention, the amount of the overhead (3A) to be held (or the amount of the overhead (3A) to be discharged) in condensation and discharge step may be regulated (or controlled) throughout the whole process based on the flow rate fluctuation of the overhead (3A) to be fed to the decanter.

That is, described above, the amount of the overhead (3A) to be fed to the decanter often widely fluctuates through a series of steps. In order to ease the flow rate fluctuation, the amount of the overhead (3A) to be held in the decanter may be adjusted.

Concrete examples of the method for adjusting (or controlling) the amount of the overhead (3A) to be held may include (1) a method in which the overhead (3A) is discharged so that the fluctuation of the amount or liquid level of the overhead (3A) to be held in the decanter may be reduced (e.g., a method shown in FIG. 1) and (2) a method in which a decanter having a buffering function is used as the decanter to ease the fluctuation of the feed amount of the overhead (3A) in the decanter (e.g., a method shown in FIG. 2). These methods may be combined.

The overhead (3A) discharged from the decanter is fed to the acetaldehyde separation step (or acetaldehyde distillation column). When the overhead (3A) is directly fed without adjustment of the flow rate, stabilized acetaldehyde separation is sometimes inhibited under the influence of the fluctuation of the amount of the overhead (3A) to be fed to the decanter. Thus, according to the present invention, the amount of the overhead (3A) to be fed to the acetaldehyde separation step (the total amount of the overhead (3A) and the methanol source) may be adjusted. As described later, when the overhead (3A) and the methanol source are mixed and then fed to the acetaldehyde separation step, strictly speaking, the total amount of the overhead (3A) and the methanol source is sometimes adjusted. However, since the feed amount of the methanol source is easily fixed (or kept constant), controlled fluctuation of the amount of the overhead (3A) leads to controlled fluctuation of the amount of the liquid object to be fed to the acetaldehyde distillation column. Therefore, also in such a manner, it is sufficient that the amount of the overhead (3A) is adjusted. Thus, even in the case where the total amount of the overhead (3A) and the methanol source is adjusted, the total of the overhead (3A) and the methanol source is sometimes referred to as the overhead (3A).

The method for adjusting or controlling the amount of the overhead (3A) to be fed to the acetaldehyde separation step may include, for example, (a) a method for circulating part of the overhead (3A) (or the total amount of the overhead (3A) and the methanol source) discharged from the decanter to a step different from the acetaldehyde separation step (particularly, at least the reactor or reaction step) (e.g., the embodiment shown in FIG. 1), (b) a method for feeding the acetaldehyde separation step with the overhead (3A) (or the total amount of the overhead (3A) and the methanol source) discharged from the decanter through a storage vessel having a buffering function (e.g., the embodiment shown in FIG. 1), and (c) a method for adjusting the amount of the overhead (3A) to be discharged from the decanter (or the total amount of the overhead (3A) and the methanol source)

to keep constant (or almost constant) (e.g., the embodiment shown in FIG. 2). These methods may be combined.

(Liquid Object to be Treated (or Liquid Object) to be Subjected to Acetaldehyde Separation Step)

As described later, in the acetaldehyde separation step (or acetaldehyde distillation column), the liquid object to be treated (or liquid object) containing the overhead (3A) is subjected to distillation. In the present invention, the liquid object to be subjected to the distillation contains a predetermined concentration of the methanol source. The distillation of the liquid object under the condition allows the increase in concentration of hydrogen iodide (and acetic acid) in the acetaldehyde distillation column to be inhibited efficiently.

It is sufficient that the liquid object contains at least the overhead (3A) (as described above, part of the overhead (3A) when the overhead (3A) is circulated). As described later, the methanol source may be added to the overhead (3A). The liquid object may contain a liquid component circulated or recycled after the acetaldehyde separation step (for example, a lower boiling point component (4A), a lower boiling point component (4A) after removing acetaldehyde, and a higher boiling point component (4B)), and others.

Usually, the liquid object mainly comprises the overhead (3A) and contains a variety of components such as methyl iodide and methyl acetate in addition to acetaldehyde and acetic acid.

The concentration of methyl iodide in the liquid object may for example be about 1 to 98% by weight (e.g., about 1 to 95% by weight), preferably about 1.5 to 95% by weight (e.g., about 10 to 90% by weight), and more preferably about 20 to 80% by weight (e.g., about 30 to 70% by weight). Moreover, the concentration of methyl iodide may for example be about not less than 60% by weight (e.g., about 70 to 98% by weight), preferably not less than 70% by weight (e.g., about 80 to 97% by weight), and more preferably not less than 85% by weight (e.g., about 87 to 95% by weight). When the lower layer portion of the overhead (3A) is mainly used as the liquid object, the concentration of methyl iodide is usually within such a range.

Further, the concentration of the methyl iodide may for example be not more than 20% by weight (e.g., about 0.1 to 15% by weight), preferably not more than 15% by weight (e.g., about 0.5 to 10% by weight), and more preferably not more than 10% by weight (e.g., about 1 to 6% by weight). When the upper layer portion of the overhead (3A) is mainly used as the liquid object, the concentration of methyl iodide is usually within such a range.

Incidentally, in terms of the inhibition of the corrosion, it is preferable that the concentration of the component (e.g., methyl iodide) producing hydrogen iodide in an equilibrium reaction in the acetaldehyde distillation column be low.

The concentration of methyl acetate in the liquid object may be selected from the range of 0.5 to 50% by weight, and may for example be about 0.5 to 30% by weight (e.g., about 1 to 25% by weight), preferably about 2 to 25% by weight (e.g., about 3 to 20% by weight), and more preferably about 3 to 15% by weight (e.g., about 4 to 10% by weight). Moreover, the concentration of methyl acetate may for example be not more than 30% by weight (e.g., about 0.1 to 25% by weight), preferably not more than 20% by weight (e.g., about 0.5 to 18% by weight), and more preferably not more than 15% by weight (e.g., about 3 to 13% by weight). When the lower layer portion of the overhead (3A) is mainly used as the liquid object, the concentration of methyl acetate is usually within such a range.

Further, the concentration of methyl acetate may for example be not more than 20% by weight (e.g., about 0.1 to 15% by weight), preferably not more than 15% by weight (e.g., about 0.5 to 10% by weight), and more preferably not more than 10% by weight (e.g., about 1 to 8% by weight). When the upper layer portion of the overhead (3A) is mainly used as the liquid object, the concentration of methyl acetate is usually within such a range.

The concentration of acetic acid in the liquid object may be selected from the range of 0.1 to 50% by weight (e.g., 0.2 to 50% by weight and preferably 0.3 to 50% by weight), and may for example be about 0.2 to 40% by weight, preferably about 0.5 to 30% by weight (e.g., about 0.8 to 25% by weight), and more preferably about 1 to 20% by weight (e.g., about 3 to 15% by weight). Moreover, the concentration of acetic acid may for example be not more than 20% by weight (e.g., about 0.1 to 15% by weight), preferably not more than 10% by weight (e.g., about 0.3 to 8% by weight), and more preferably not more than 8% by weight (e.g., about 0.5 to 5% by weight). When the lower layer portion of the overhead (3A) is mainly used as the liquid object, the concentration of acetic acid is usually within such a range.

Further, the concentration of acetic acid may for example be not more than 50% by weight (e.g., about 1 to 45% by weight), preferably not more than 40% by weight (e.g., about 5 to 35% by weight), and more preferably not more than 30% by weight (e.g., about 8 to 25% by weight). When the upper layer portion of the overhead (3A) is mainly used as the liquid object, the concentration of acetic acid is usually within such a range.

The concentration of water in the liquid object may be selected from the range of 0.05 to 95% by weight, and may for example be about 0.1 to 90% by weight (e.g., about 0.2 to 80% by weight), preferably about 0.5 to 80% by weight (e.g., about 0.8 to 75% by weight), and more preferably about 1 to 75% by weight (e.g., about 1.5 to 70% by weight). Moreover, the concentration of water may for example be not more than 5% by weight (e.g., about 0.01 to 3% by weight), preferably not more than 3% by weight (e.g., about 0.05 to 2% by weight), and more preferably not more than 2% by weight (e.g., about 0.1 to 1% by weight). When the lower layer portion of the overhead (3A) is mainly used as the liquid object, the concentration of water is usually within such a range.

Further, the concentration of water may for example be not less than 40% by weight (e.g., about 45 to 95% by weight), preferably not less than 50% by weight (e.g., about 55 to 90% by weight), and more preferably not less than 60% by weight (e.g., about 65 to 80% by weight). When the upper layer portion of the overhead (3A) is mainly used as the liquid object, the concentration of water is usually within such a range.

The concentration of hydrogen iodide in the liquid object may be selected from the range of 1 to 2000 ppm (e.g., 1 to 1000 ppm and preferably 5 to 1000 ppm) on the basis of weight, and may for example be about 3 to 1500 ppm, preferably about 4 to 1000 ppm, and more preferably about 5 to 800 ppm (e.g., about 7 to 600 ppm) and may usually be about 1 to 500 ppm [e.g., about 1 to 300 ppm, preferably about 5 to 200 ppm (e.g., about 5 to 150 ppm), more preferably about 10 to 120 ppm, and particularly about 15 to 100 ppm]. Incidentally, the concentration of hydrogen iodide in the liquid object may for example be about 3 to 100 ppm and preferably about 5 to 80 ppm (e.g., about 5 to 50 ppm) on the basis of weight. When the lower layer portion of the condensed overhead (3A) is mainly subjected to the acetaldehyde separation step, the concentration of hydrogen iodide is usually within such a range. Moreover, the concentration of hydrogen iodide in the liquid object may for example be about 30 to 150 ppm and preferably about 50 to 100 ppm on the basis of weight. When the upper layer portion of the condensed overhead (3A) is mainly subjected to the acetaldehyde separation step, the concentration of hydrogen iodide is usually within such a range.

The concentration of hydrogen iodide may be measured directly or measured (or calculated) indirectly. For example, the concentration of the iodide ion derived from the iodide salt [for example, an iodide derived from the co-catalyst such as LiI, and a metal iodide (e.g., an iodide of a corroded metal (such as Fe, Ni, Cr, Mo, or Zn) produced in the process of the acetic acid production)] may be subtracted from the total concentration of iodide ions ($I^-$) to determine (or calculate) the concentration of hydrogen iodide.

The concentration of acetaldehyde in the liquid object may for example be about 0.001 to 5% by weight, preferably about 0.005 to 3% by weight, and more preferably about 0.01 to 1% by weight and may usually be about 0.02 to 0.7% by weight (e.g., about 0.03 to 0.6% by weight). Incidentally, the concentration of acetaldehyde in the liquid object may for example be 200 to 6000 ppm and preferably about 400 to 4000 ppm on the basis of weight. When the lower layer portion of the condensed overhead (3A) is mainly subjected to the acetaldehyde separation step, the concentration of acetaldehyde is usually within such a range. Moreover, the concentration of acetaldehyde in the liquid object may for example be about 500 to 20000 ppm and preferably about 1000 to 16000 ppm on the basis of weight. When the upper layer portion of the condensed overhead (3A) is mainly subjected to the acetaldehyde separation step, the concentration of acetaldehyde is usually within such a range.

The liquid object contains at least one methanol source selected from the group consisting of methanol and dimethyl ether. The methanol source may be methanol alone, dimethyl ether alone, or combination of methanol and dimethyl ether. Incidentally, the methanol source also includes methanol obtained by hydrolysis of methyl acetate. For the combination of methanol and dimethyl ether, the ratio (weight ratio) of methanol relative to dimethyl ether [the former/the latter] may be about 99.9/0.1 to 0.1/99.9 (e.g., about 99/1 to 1/99), preferably about 95/5 to 5/95, and more preferably about 90/10 to 10/90 (e.g., about 85/15 to 15/85). Incidentally, when the methanol source contains one component (either methanol or dimethyl ether) in a relatively large quantity, the ratio (weight ratio) of one component relative to the other component [the former/the latter] may be about 99.9/0.1 to 30/70 (e.g., about 99.5/0.5 to 40/60), preferably about 99/1 to 45/55 (e.g., about 98.5/1.5 to 50/50), more preferably about 98/2 to 55/45 (e.g., about 97/3 to 60/40), and particularly about 96/4 to 65/35 (e.g., about 95/5 to 70/30).

The concentration of the methanol source in the liquid object may be selected from the range of 0.1 to 50% by weight (e.g., 0.2 to 50% by weight), and may for example be about 0.1 to 40% by weight (e.g., about 0.2 to 30% by weight), preferably about 0.2 to 25% by weight, more preferably about 0.2 to 20% by weight (e.g., about 0.5 to 18% by weight), and particularly about 0.7 to 17% by weight (e.g., about 1 to 15% by weight and preferably about 2 to 15% by weight) and may usually be about 1 to 30% by weight (e.g., about 2 to 25% by weight).

Incidentally, the concentration of the methanol source in the liquid object may be about 0.1 to 35% by weight (e.g., about 0.1 to 28% by weight), preferably about 0.15 to 21% by weight, more preferably about 0.2 to 17% by weight (e.g., about 0.5 to 13% by weight), and particularly about 0.6 to 12% by weight (e.g., about 0.7 to 10% by weight). Such a concentration is preferable, in particular, when the methanol source contains dimethyl ether in a large quantity, or other cases.

Incidentally, the concentration of the methanol source in the liquid object may for example be about 0.1 to 20% by weight and preferably about 0.2 to 15% by weight (e.g., about 0.5 to 13% by weight). When the lower layer portion of the condensed overhead (3A) is mainly subjected to the acetaldehyde separation step, the concentration of the methanol source is usually within such a range.

Moreover, the concentration of the methanol source in the liquid object may for example be about 0.3 to 50% by weight (e.g., about 0.5 to 40% by weight) and preferably about 1 to 30% by weight. When the upper layer portion of the condensed overhead (3A) is mainly subjected to the acetaldehyde separation step, the concentration of the methanol source is usually within such a range.

Moreover, in the liquid object, the ratio of the methanol source (in terms of methanol) relative to 1 mol of the total amount of acetic acid and hydrogen iodide in the liquid object (or the overhead (3A)) may be selected from the range of about 0.1 to 40 mol, and may for example be about 0.1 to 20 mol (e.g., about 0.3 to 15 mol), preferably about 0.4 to 10 mol (e.g., about 0.5 to 10 mol), more preferably about 0.7 to 7 mol (e.g., about 1 to 5 mol), and particularly about 1.1 to 4 mol (e.g., about 1.2 to 3 mol) and may usually be about 1 to 20 mol (e.g., about 1.5 to 5 mol). Incidentally, the above-mentioned ratio is expressed in terms of methanol. That is, for the use of dimethyl ether as the methanol source, since 2 mol of methanol is produced by hydrolysis of 1 mol of dimethyl ether, the ratio is calculated as 2 mol of methanol per mol of dimethyl ether.

Further, in the liquid object, the ratio of the methanol source (in terms of methanol) relative to 1 mol of hydrogen iodide in the liquid object may be not less than 70 mol [for example, not less than 80 mol (e.g., about 100 to 300000 mol)], preferably not less than 200 mol (e.g., about 300 to 200000 mol), more preferably not less than 500 mol (e.g., about 700 to 100000 mol), particularly not less than 1000 mol (e.g., about 1500 to 80000 mol), and usually about 300 to 100000 mol (e.g., about 500 to 70000 mol and preferably about 1000 to 50000 mol).

Furthermore, in the liquid object, the ratio of the methanol source (in terms of methanol) relative to 1 mol of acetic acid in the liquid object may be selected from the range of about 0.1 to 40 mol, and may for example be about 0.1 to 20 mol (e.g., about 0.3 to 15 mol), preferably about 0.4 to 10 mol (e.g., about 0.5 to 10 mol), more preferably about 0.7 to 7 mol (e.g., about 1 to 5 mol), and particularly about 1.1 to 4 mol (e.g., about 1.2 to 3 mol) and may usually be about 1 to 20 mol (e.g., about 1.5 to 5 mol).

Moreover, the ratio of the methanol source (in terms of methanol) relative to 1 mol of acetic acid in the liquid object may be about 0.1 to 40 mol (e.g., about 0.3 to 35 mol), preferably about 0.4 to 30 mol (e.g., about 0.5 to 25 mol), more preferably about 0.7 to 20 mol (e.g., about 1 to 15 mol), and particularly about 1.1 to 10 mol (e.g., about 1.2 to 7 mol). When the lower layer portion of the condensed overhead (3A) is mainly subjected to the acetaldehyde separation step, the concentration of the methanol source is usually within such a range. Further, the ratio of the methanol source (in terms of methanol) relative to 1 mol of acetic acid in the liquid object may be about 0.05 to 20 mol (e.g., about 0.1 to 15 mol), preferably about 0.2 to 10 mol (e.g., about 0.3 to 8 mol), more preferably about 0.5 to 6 mol (e.g., about 1 to 5 mol), and particularly about 1.1 to 4 mol (e.g., about 1.2 to 3 mol). When the upper layer portion of the condensed overhead (3A) is mainly subjected to the acetaldehyde separation step, the concentration of the methanol source is usually within such a range.

The concentration of the methanol source in the liquid object may be adjusted with the reaction or the feed amount. The concentration of the methanol source can usually be adjusted by adding or mixing the methanol source and/or methyl acetate to the overhead (3A) inside or outside the acetaldehyde distillation column. Typically, the process of the present invention may comprise a step (sometimes referred to as an addition step or a mixing step) for adding or mixing the methanol source (methanol and/or dimethyl ether) and/or methyl acetate to the overhead (3A) to be fed to the acetaldehyde distillation column. As described above, since methanol can be produced from methyl acetate, methyl acetate can also be added to or mixed with the overhead (3A) as far as the concentration of the methanol source in the acetaldehyde distillation column can be adjusted. In particular, at least the methanol source may be added to the overhead (3A).

The methanol source can be mixed with the overhead (3A) at any stage of the reaction system as far as the methanol source can be distilled by the acetaldehyde distillation column together with the overhead (3A) separated in the acetic acid collection step. The methanol source may be mixed with the overhead (3A) in the acetaldehyde distillation column. In particular, from the viewpoint that the increase in concentration of hydrogen iodide (and concentration of acetic acid) in the acetaldehyde distillation column is efficiently inhibited, the methanol source and/or methyl acetate may be added or mixed in the following manner (A) and/or manner (B):

(A) the methanol source is added to or mixed with the overhead (3A) before the overhead (3A) is fed to the acetaldehyde distillation column (e.g., the embodiment of FIG. 1), (B) in the acetaldehyde distillation column, the methanol source and/or methyl acetate is added to or mixed with the overhead (3A) at the same height level or position [for example, the same plate (or site)] as a height level or position at which the overhead (3A) is fed or at a height level [e.g., a plate (or site)] upper than (or at an upper height level over) the height level at which the overhead (3A) is fed (e.g., the embodiment of FIG. 1 and the embodiment of FIG. 2).

In the manner (A), the mixing position of the methanol source to the overhead (3A) is not particularly limited to a specific one as far as the methanol source is mixed with the overhead (3A) before the overhead (3A) is fed to the acetaldehyde distillation column. For example, the methanol source may be mixed with the overhead (3A) prior to feeding to the decanter, after discharge from the decanter, or after discharge from the buffer tank (e.g., embodiments of FIG. 1 and FIG. 2). The methanol source and/or methyl acetate may be mixed at a plurality of positions. Representatively, the methanol source and/or methyl acetate is usually added after discharge from the decanter (when part of the overhead (3A) is circulated, after the circulation). In particular, it is preferable that the methanol source and/or methyl acetate be mixed with the overhead (3A) in a line from discharge from the decanter to feeding to the acetaldehyde distillation column [a line from the decanter (if necessary, through a storage vessel having a buffering function) to the acetaldehyde removal column)].

The time from when the overhead (3A) and the methanol source and/or methyl acetate are mixed till when the mixture is fed to the acetaldehyde distillation column (the retention time of the methanol source and/or methyl acetate) may be selected from the range of not less than 1 second (e.g., 3 seconds to 40 minutes), and for example be not less than 5 seconds (e.g., about 7 seconds to 35 minutes), preferably not less than 10 seconds (e.g., about 10 seconds to 30 minutes), and more preferably about 15 seconds to 20 minutes (e.g., about 20 seconds to 10 minutes) and may usually be about 10 seconds to 5 minutes [for example, about 10 seconds to 3 minutes (e.g., about 10 seconds to 1 minute)]. The increase in concentration of hydrogen iodide or acetic acid in the acetaldehyde distillation column is further easily inhibited by regulating the retention time in such a range (in particular, in combination with the after-mentioned the liquid temperature).

Moreover, in the manner (B), the methanol source and/or methyl acetate may be mixed at the same position as a plate at which the overhead (3A) is fed or an upper plate than that plate, and is usually mixed at a position lower than the column top (a position which is not the column top).

For the combination of the manner (A) with the manner (B), it is sufficient that the total amount of the methanol source and/or methyl acetate to be mixed is adjusted at each mixing position so that the total amount may be in the above-mentioned range in the acetaldehyde distillation column.

The temperature (liquid temperature) of the overhead (3A) to be fed to the acetaldehyde distillation column (the mixture of the overhead (3A) and the methanol source, when the methanol source and/or methyl acetate is added to the overhead (3A)) may for example be about 10 to 100° C., preferably about 15 to 95° C. (e.g., about 20 to 90° C.), and more preferably about 25 to 85° C. (e.g., about 30 to 80° C.) and may usually be about 20 to 100° C. (e.g., about 30 to 85° C.).

In particular, since such a range of the liquid temperature (that is, the liquid temperature of the mixture of the overhead (3A) and the methanol source) in the combination with the manner (A) probably allows the reaction of the methanol source with hydrogen iodide or acetic acid to proceed to some extent before feeding the overhead (3A) to the acetaldehyde distillation column or probably promotes such a reaction in the acetaldehyde distillation column, the increase in concentration of hydrogen iodide or acetic acid in the acetaldehyde distillation column can further efficiently inhibited.

(Acetaldehyde Separation Step)

In the acetaldehyde separation step, the liquid object containing the overhead (3A) fed to the acetaldehyde distillation column (removal column or separation column) is separated into a lower boiling point component (4A) containing acetaldehyde and a higher boiling point component (4B) by distillation. As described above, the liquid object is subjected to distillation as a liquid object to be treated containing a predetermined concentration of the methanol source. That is, in the acetaldehyde separation step, the liquid object is distilled and separated into the lower boiling point component (4A) and the higher boiling point component (4B). Prior to the separation of acetaldehyde, an off gas component may be removed from the overhead (3A) beforehand by using a condenser, a cooler, or others.

As the acetaldehyde distillation column, a conventional distillation column, for example, a plate column, a packed column, and a flash distillation column, may be used. A distillation column such as a plate column or a packed column may usually be employed. The material of (or for forming) the acetaldehyde distillation column is not particularly limited to a specific one, and may be a metal, a ceramic, and others. In particular, according to the present invention, since the increase in concentration of hydrogen iodide (and acetic acid) inside the distillation column is significantly inhibited, the corrosion of the distillation column can also be inhibited at a high level. Thus, as the acetaldehyde distillation column in the present invention, there may be used not only a distillation column made of an expensive material having a high corrosion resistance (such as zirconium) but also a distillation column made of a relatively inexpensive material, for example, an alloy [for example, a transition-metal-based alloy such as an iron-based alloy (or an alloy containing iron as a main component, e.g., a stainless steel (including a stainless steel containing chromium, nickel, molybdenum and others)), a two-phase iron-based alloy (e.g., a two-phase (or duplex) stainless steel), a nickel-based alloy (or an alloy containing nickel as a main component, e.g., HASTELLOY (brand name) and INCONEL (brand name)), or a cobalt-based alloy (or an alloy containing cobalt as a main component)].

The temperature (the temperature of the column top) and the pressure (the pressure of the column top)) in the acetaldehyde distillation column may be selected depending on the species of the distillation column and others, and is not particularly limited to a specific one as far as the lower boiling point component (4A) containing at least acetaldehyde and the higher boiling point component (4B) are separable from the overhead (3A) or the liquid object (or process solution) by utilizing difference between acetaldehyde and other components (particularly methyl iodide) in boiling point.

For example, the column top pressure is about 10 to 1000 kPa, preferably about 10 to 700 kPa, and more preferably about 100 to 500 kPa in terms of absolute pressure.

The inner temperature of the column may for example be about 10 to 150° C., preferably about 30 to 140° C., and more preferably about 40 to 130° C. and may usually be about 30 to 100° C. (e.g., about 50 to 90° C.). Moreover, the temperature of the column top may for example be about 10 to 100° C., preferably about 30 to 120° C., and more preferably about 40 to 100° C. Further, the temperature of the column bottom may for example be about 30 to 150° C., preferably about 50 to 130° C., and more preferably about 60 to 120° C.

The number (theoretical number) of plates of the distillation column may for example be about 5 to 150, preferably about 10 to 120, and more preferably about 20 to 100 and may usually be about 30 to 120 (e.g., about 40 to 100).

In the acetaldehyde distillation column, the reflux ratio may be selected from about 1 to 1000, preferably about 10 to 800, more preferably about 50 to 600 (e.g., about 100 to 500), and particularly about 150 to 400 (e.g., about 200 to 350) depending on the above-mentioned theoretical number of plates.

In such a way, the increase in concentration of hydrogen iodide or acetic acid in the acetaldehyde distillation column can be inhibited by the distillation in the presence of the methanol source. For example, in the continuous reaction, the concentration of hydrogen iodide in the acetaldehyde distillation column (column top and/or column bottom) is not more than 100 ppm (e.g., about 0 or detection limit to 70 ppm), preferably not more than 50 ppm (e.g., about 0 or detection limit to 30 ppm), more preferably not more than 10 ppm (e.g., about 0 or detection limit to 5 ppm), and particularly not more than 3 ppm (e.g., about 0 or detection limit to 1 ppm).

Moreover, in the continuous reaction, the concentration of acetic acid in the acetaldehyde distillation column (column top and/or column bottom) may for example be not more than 50% by weight (e.g., 0 (or not more than detection limit, the same applies in others) to 30% by weight), preferably about 0 to 10% by weight (e.g., about 0.001 to 5% by weight), more preferably about 0 to 3% by weight (e.g., about 0.01 to 2% by weight), and particularly about 0.005 to 1% by weight.

Incidentally, the concentration of acetic acid in the acetaldehyde distillation column (column top and/or column bottom) may be not more than 10% by weight (e.g., about 0 to 7% by weight), preferably not more than 7% by weight (e.g., about 0 to 6% by weight), and more preferably not more than 5% by weight (e.g., about 0 to 4% by weight). When the lower layer portion of the condensed overhead (3A) is mainly subjected to the acetaldehyde separation step, the concentration of acetic acid is usually within such a range. Moreover, the concentration of acetic acid in the acetaldehyde distillation column (column top and/or column bottom) may be not more than 30% by weight (e.g., about 0 to 25% by weight), preferably not more than 15% by weight (e.g., about 0 to 10% by weight), and more preferably not more than 8% by weight (e.g., about 0 to 5% by weight). When the upper layer portion of the condensed overhead (3A) is mainly subjected to the acetic acid separation step, the concentration of acetaldehyde is usually within such a range.

The higher boiling point component (4B) is separated as a separated solution (bottom fraction or column bottom fraction) containing a useful component methyl iodide from the acetaldehyde distillation column.

(Recycling Step)

The higher boiling point component (4B) practically contains a useful component such as methyl iodide. After separation, the higher boiling point component (4B) may be recovered as it is or recycled to a step from the reaction system to the acetaldehyde separation. That is, the process of the present invention may further comprise a recycling step for recycling the higher boiling point component (4B) as a separated solution to a step from the reaction system to the acetaldehyde separation.

In the recycling step, the higher boiling point component (4B) as a separated solution is recycled. The recycling of the separated solution (or higher boiling point component (4B)) is not particularly limited to a specific one as far as the recycling step is placed from the reaction system to the acetaldehyde separation. The step may be any of the reaction step (or reactor), the flash distillation step (or flash distillation column), and the acetic acid collection step (or distillation column). As the embodiment of the figure, the higher boiling point component (4B) may be recycled to the acetaldehyde distillation column, or may be recycled to a combination of these steps. The separated solution (or higher boiling point component (4B)) after acetaldehyde separation is usually recycled to at least the reactor.

The separated solution (or higher boiling point component (4B)) may be recycled directly or recycled through a storage vessel having a buffering function (e.g., a buffer tank). Use of the storage vessel having a buffering function eases the flow rate fluctuation in the storage vessel and allows easy recycling of the separated solution at a constant or almost constant flow rate, even if the flow rate of the separated solution fluctuates. Thus the storage vessel can reduce the influence of the flow rate fluctuation on the recycling step.

The storage vessel having a buffering function may be selected based on the degree of the flow rate fluctuation, in the same manner as in the condensation step, and may be selected based on the desired retention time of the separated solution. In the storage vessel, the retention time of the separated solution is not particularly limited to a specific one, and may for example be not less than 3 minutes (e.g., about 4 minutes to 3 hours), preferably not less than 6 minutes (e.g., about 8 to 60 minutes), and more preferably not less than 12 minutes (e.g., about 15 to 40 minutes).

When the separated solution is recycled through the storage vessel having a buffering function, the fluctuation of the flow rate of the separated solution (higher boiling point component (4B)) can be decreased.

The separated lower boiling point component (4A) containing acetaldehyde may be discharged as it is. Since the lower boiling point component (4A) sometimes contains a useful component such as methyl iodide, methyl iodide (or a component containing methyl iodide, for example, a component containing methyl iodide, methyl acetate, and others) may be collected from the lower boiling point component (4A) and recycled.

The method for separating each of acetaldehyde and methyl iodide (or a component containing methyl iodide) from the lower boiling point component (4A) is not particularly limited to a specific one, and may include a conventional method (for example, extraction, distillation). Representative examples of the method may include (i) a method for separating each of methyl iodide and acetaldehyde by distilling the lower boiling point component (4A), (ii) a method for separating each of methyl iodide and acetaldehyde by water extraction, which takes advantage of the miscibility of acetaldehyde with water and the immiscibility of methyl iodide with water. From the viewpoint of the inhibition of production of metaldehyde or others, the water extraction (ii) is preferred. According to the method, since the increase in proton concentration in the distillation solution due to ester degradation or others inhibits production of paraldehyde and metaldehyde, acetaldehyde can efficiently be condensed to a high level and removed.

The extraction temperature and the extraction time are not particularly limited to specific ones. For example, the extraction may be carried out at a temperature of 0° C. to 100° C. for about 1 second to 1 hour. The extraction pressure is not particularly limited to a specific one, and an advantageous condition can be selected because of costs, and others. As the extractor, for example, there may be used a combination of a mixer with a settler, a combination of a static mixer with a decanter, an RDC (rotated disk contactor), a Karr column, a spray column, a packed column, a perforated plate column, a baffled column, a pulse column, and others.

The recycling of methyl iodide (or a component containing methyl iodide) is not particularly limited to a specific one as far as the recycle step is placed from the reaction system to the acetaldehyde separation. Methyl iodide may be recycled to any of the reaction step (or reactor), the flash distillation step (or flash distillation column), and the acetic acid collection step (or distillation column). As the embodiment of the figure, methyl iodide may be recycled (recycled as the higher boiling point component (4B)) to the acetaldehyde-separating column, or may be recycled to a combination of these steps.

EXAMPLES

The following examples are intended to describe this invention in further detail and should by no means be interpreted as defining the scope of the invention.

Comparative Examples 1 to 4 and Examples 1 to 6

When the production process of acetic acid described in FIG. 1 was applied, the change of the corrosion state in the presence of methanol was observed. Specifically, methyl iodide, water, methyl acetate, acetic acid, lithium iodide, rhodium was fed to the reactor 1, and methanol was allowed to react with carbon monoxide. The reaction solution was withdrawn from the reactor 1 and fed to a flasher. In the flasher 2, the volatile component (2A) was fed to the splitter column 3, and the low-volatile component (2B) was directly recycled to the reactor 1. In the splitter column 3, the volatile component (2A) was separated by distillation into the overhead (3A), the stream containing acetic acid, and the higher boiling point stream (3C). The stream containing acetic acid (3B) was withdrawn by side cut, and the higher boiling point stream (3C) was directly recycled to the reactor 1. The overhead (3A) was fed to the decanter 4 and separated into an upper layer and a lower layer in the decanter 4. In the decanter 4, the liquid level of the decanter 4 was kept constant by adjusting the amount flowing to the lines 17 and 18 and the retention time. Then as a solution discharged from the decanter 4 and to be fed to the acetaldehyde removal column 6, a liquid object to be treated having a composition shown in Table 1 was obtained. In Comparative Examples 1 and 3 and Examples 1, 3, and 5, a lower layer portion of the overhead (3A) in the decanter 4 was used; in Comparative Examples 2 and 4 and Examples 2, 4, and 6, an upper layer portion of the overhead (3A) in the decanter 4 was used. In Examples 1 and 2, the concentration of methanol in the liquid object was adjusted by feeding methanol through the line 51.

The liquid object shown in Table 1 and test pieces of different materials (each size: 36 mm×25 mm×2.5 mm) were put in a 500-ml autoclave [made of HASTELLOYB2 (HB2) manufactured by Oda Koki Co., Ltd.], and the autoclave was sealed. The inner pressure of the autoclave was increased to 0.05 MPa with $N_2$ at a room temperature, and then the inner temperature of the autoclave was increased to 85° C. Under this circumstance, the inner pressure of the autoclave was increased to 0.14 MPa. By maintaining the autoclave for 100 hours in this state, the acetaldehyde separation step (the state in the acetaldehyde removal column 6) in the continuous production process of acetic acid was artificially reproduced. Thereafter, the corrosion of each test piece was observed. The corrosion test was evaluated on the basis of the following criteria in Comparative Examples 1 to 2 and Examples 1 to 2 and evaluated on the observed corrosion amount in Comparative Examples 3 to 4 and Examples 3 to 6.

"A": Test piece is not corroded at all.
"B": Test piece is hardly corroded.
"C": Test piece is slightly corroded.
"D": Test piece is significantly corroded.

The composition (formulation) of each liquid object is shown in Table 1, and the results are shown in Table 2. The composition (formulation) of each liquid object after maintaining for 100 hours (then after cooling), that is, treated liquid object, is also shown in Table 2. Incidentally, when methanol was added, the liquid object sometimes contained a lower boiling point component such as dimethyl ether or a hydrocarbon component (accordingly the sum of components described in Tables was not 100% by weight). The concentration of dimethyl ether in the treated liquid object was about 0.5 to 2% by weight higher than that in the liquid object. In Tables 1 and 2, "ppm" represents a concentration on the basis of weight, "wt %" means % by weight, "t" represents less than 0.1% by weight, "ND" represents not detectable (detection limit), "Ac" represents acetic acid, "MA" represents methyl acetate, "MeOH" represents methanol, "MeI" represents methyl iodide, "AD" represents acetaldehyde, "HC" represents a nickel-based alloy (HASTELLOY C manufactured by Oda Koki Co., Ltd.), "SUS" represents a stainless steel (SUS316 manufactured by Umetoku Inc.), "NAS64" represents a two-phase stainless steel (NAS64 manufactured by Umetoku Inc.), and "NAS354N" represents a stainless steel (NAS354N manufactured by Umetoku Inc.), and "mm/Y" means the corrosion rate of the test piece per year (the decreased thickness (mm) of the test piece per year). The concentration of the iodide ion derived from the iodide salt was subtracted from the total concentration of iodide ions ($I^-$) to calculate the concentration of hydrogen iodide.

As apparent from the tables, the production or increased concentration of hydrogen iodide (HI) and the corrosion of the test piece were inhibited by adjusting the composition of the liquid in the acetaldehyde removal column to specific components and specific proportions.

INDUSTRIAL APPLICABILITY

The production process of the present invention is extremely useful as a process for producing acetic acid while efficiently inhibiting the increase in concentration of hydrogen iodide (in particular, hydrogen iodide and acetic acid) in the acetaldehyde distillation column.

DESCRIPTION OF REFERENCE NUMERALS

1 . . . Reactor
2 . . . Flasher (evaporator)
3 . . . Splitter column
4 . . . Decanter
4A . . . Decanter having buffering function
5, 7 . . . Buffer tank
6 . . . Acetaldehyde removal column

TABLE 1

| | Liquid object to be treated | | | | | | | | |
|---|---|---|---|---|---|---|---|---|---|
| | Ac wt % | MA wt % | MeOH wt % | HI ppm | MeI wt % | $H_2O$ wt % | AD ppm | MeOH/ (HI + Ac) Molar ratio | MeOH/HI Molar ratio |
| Comparative Example 1 | 2 | 5 | t | 10 | 90 | 0.5 | 1300 | 0 | 0 |
| Comparative Example 2 | 20 | 4 | t | 30 | 3 | 70 | 4000 | 0 | 0 |
| Example 1 | 2 | 4.5 | 5 | 10 | 85.5 | 0.5 | 1300 | 5 | 20000 |
| Example 2 | 16 | 3.2 | 20 | 24 | 2.4 | 56 | 4000 | 1.9 | 27000 |
| Comparative Example 3 | 2.1 | 4.8 | t | 12 | 91 | 0.6 | 1150 | 0 | 0 |
| Comparative Example 4 | 20.9 | 4.2 | t | 35 | 2.8 | 69.5 | 4200 | 0 | 0 |
| Example 3 | 2.0 | 4.7 | 5.1 | 13 | 86 | 0.5 | 1100 | 4.8 | 16000 |
| Example 4 | 16.5 | 3.5 | 19.8 | 26 | 2.3 | 56.5 | 3400 | 2.2 | 30000 |
| Example 5 | 1.8 | 4.4 | 11 | 12 | 81.5 | 0.4 | 1100 | 11 | 18000 |
| Example 6 | 18.5 | 3.9 | 10.5 | 24 | 2.6 | 63.8 | 3800 | 1.1 | 37000 |

TABLE 2

| | Treated liquid object | | | | | | | Corrosion test | | | |
|---|---|---|---|---|---|---|---|---|---|---|---|
| | Ac wt % | MA wt % | MeOH wt % | HI ppm | MeI wt % | $H_2O$ wt % | AD ppm | HC mm/Y | SUS mm/Y | NAS64 mm/Y | NAS354N mm/Y |
| Comparative Example 1 | 2 | 5 | 0.1 | 12 | 90 | 0.5 | 600 | B | D | D | D |
| Comparative Example 2 | 20 | 4 | t | 33 | 3 | 70 | 2000 | C | D | D | D |
| Example 1 | 0.1 | 7 | 4 | ND | 85.5 | 1 | 600 | A | A | A | A |
| Example 2 | 0.2 | 23 | 11 | ND | 2.4 | 61 | 2000 | A | A | A | A |
| Comparative Example 3 | 2.1 | 4.8 | t | 12 | 91 | 0.6 | 920 | 0.05 | 0.12 | 0.09 | 0.1 |
| Comparative Example 4 | 20.9 | 4.2 | t | 35 | 2.8 | 69.5 | 3800 | 0.10 | 0.21 | 0.15 | 0.13 |
| Example 3 | 1.0 | 5.0 | 3.0 | ND | 85.5 | 1.1 | 900 | less than 0.03 | less than 0.03 | less than 0.03 | less than 0.03 |
| Example 4 | 9.5 | 10.8 | 11.3 | ND | 2.3 | 58.4 | 2500 | less than 0.03 | less than 0.03 | less than 0.03 | less than 0.03 |
| Example 5 | 0.5 | 6.0 | 7.1 | ND | 80.8 | 1.5 | 930 | less than 0.03 | less than 0.03 | less than 0.03 | less than 0.03 |
| Example 6 | 14.9 | 7.8 | 8.3 | ND | 2.3 | 64.9 | 2900 | less than 0.03 | less than 0.03 | less than 0.03 | less than 0.03 |

8 . . . Extraction apparatus
9 . . . Hold tank
51, 52 . . . Line for feeding Methanol source (methanol and/or dimethyl ether)

The invention claimed is:

[1. A process for producing acetic acid, which comprises:

a reaction step for continuously allowing methanol to react with carbon monoxide in the presence of a catalyst system comprising a metal catalyst, a halide salt, and methyl iodide in a carbonylation reactor, a flash evaporation step for continuously feeding a flasher with a reaction mixture from the reactor to separate a volatile component (2A) containing product acetic acid, methyl acetate, methyl iodide and water, and a low-volatile component (2B) containing the metal catalyst and the halide salt, an acetic acid collection step for feeding a distillation column with the volatile component (2A), and separating an overhead (3A) containing methyl iodide, acetic acid, methyl acetate, water, by-product acetaldehyde, and hydrogen iodide, and a stream (3B) containing acetic acid to collect acetic acid, and an acetaldehyde separation step for feeding an acetaldehyde distillation column with at least part of the overhead (3A) and distilling a liquid object to be treated containing the overhead (3A) to separate a lower boiling point component (4A) containing acetaldehyde and a higher boiling point component (4B), wherein, in the acetaldehyde separation step, the liquid object contains at least one methanol source selected from the group consisting of methanol and dimethyl ether in a concentration of 2 to 50% by weight.]

[2. A process according to claim 1, wherein, in the liquid object, the proportion of methyl iodide is 1 to 98% by weight, the proportion of methyl acetate is 0.5 to 50% by weight, the proportion of acetic acid is 0.2 to 50% by weight, the proportion of water is 0.05 to 95% by weight, and the proportion of hydrogen iodide is 1 to 1000 ppm on the basis of weight.]

[3. A process according to claim 1, wherein the concentration of the methanol source in the liquid object is 2 to 40% by weight.]

[4. A process according to claim 1, wherein the concentration of the methanol source in the liquid object is 2 to 25% by weight.]

[5. A process according to claim 1, wherein, in the liquid object, the concentration of acetic acid is 0.3 to 50% by weight, the ratio of the methanol source (in terms of methanol) is 0.1 to 40 mol relative to 1 mol a total amount of acetic acid and hydrogen iodide.]

[6. A process according to claim 1, wherein the ratio of the methanol source (in terms of methanol) in the liquid object is not less than 80 mol relative to 1 mol of hydrogen iodide.]

[7. A process according to claim 1, wherein, in the liquid object, the concentration of acetic acid is 0.5 to 50% by weight, the concentration of hydrogen odide is 5 to 1000 ppm, and the ratio of the methanol source (in terms of methanol) is 1 to 20 mol relative to 1 mol a a total amount of acetic acid and hydrogen iodide.]

[8. A process according to claim 1, wherein the concentration of the methanol source in the liquid object is adjusted by adding or mixing the methanol source and/or methyl acetate in the following manner (A) and/or manner (B):

(A) the methanol source and/or methyl acetate is added to or mixed with the overhead (3A) before the overhead (3A) is fed to the acetaldehyde distillation column, (B) in the acetaldehyde distillation column, the methanol source and/or methyl acetate is added to or mixed with the overhead (3A) at the same height level as a height level at which the overhead (3A) is fed or at a height level upper than the height level at which the overhead (3A) is fed.]

[9. A process according to claim 8, wherein, in the manner (A), a temperature of a mixture containing the overhead (3A) and the methanol source and/or methyl acetate is regulated to 20 to 100° C., and a time from when the overhead (3A) and the methanol source and/or methyl acetate are mixed till when the mixture is fed to the acetaldehyde distillation column is regulated to not less than 5 seconds; and the concentration of the methanol source is adjusted in at least the manner (A).]

[10. A process according to claim 8, wherein, in the manner (A), a temperature of a mixture containing the overhead (3A) and the methanol source and/or methyl acetate is regulated to 30 to 85° C., and a time from when the overhead (3A) and the methanol source and/or methyl acetate are mixed till when the mixture is fed to the acetaldehyde distillation column is regulated to not less than 10 seconds; and the concentration of the methanol source is adjusted in at least the manner (A).]

[11. A process according to claim 1, wherein the material of the acetaldehyde distillation column comprises an iron-based alloy.]

[12. A process according to claim 1, wherein the material of the acetaldehyde distillation column comprises a stainless steel or a two-phase stainless steel.]

*13. A process for producing acetic acid comprising:*

*a reaction step comprising continuously allowing methanol to react with carbon monoxide in the presence of a catalyst system comprising a metal catalyst, a halide salt, and methyl iodide in a carbonylation reactor;*

*a flash evaporation step comprising continuously feeding a flasher with a reaction mixture from the reactor to separate a volatile component (2A) containing product acetic acid, methyl acetate, methyl iodide and water, and a low-volatile component (2B) containing the metal catalyst and the halide salt;*

*an acetic acid collection step comprising feeding a distillation column with the volatile component (2A), and separating an overhead (3A) containing methyl iodide, acetic acid, methyl acetate, water, by-product acetaldehyde, and hydrogen iodide, and a stream (3B) containing acetic acid to collect acetic acid;*

*an acetaldehyde separation step comprising feeding an acetaldehyde distillation column with at least part of the overhead (3A) and distilling a liquid object to be treated containing the overhead (3A) to separate a lower boiling point component (4A) containing acetaldehyde and a higher boiling point component (4B); and*

*a condensation and discharge step comprising temporarily holding the overhead (3A) in a decanter while condensing, and then discharging at least a part of the overhead (3A) from the decanter to subject to the acetaldehyde separation step;*

*wherein, in the acetaldehyde separation step, the liquid object contains at least one methanol source selected from the group consisting of methanol and dimethyl ether in a concentration of 2 to 50% by weight;*

*wherein, in the liquid object, the proportion of methyl iodide is 1 to 95% by weight, the proportion of methyl acetate is 0.5 to 50% by weight, the proportion of acetic acid is 0.2 to 50% by weight, the proportion of water*

*is 0.05 to 95% by weight, and the proportion of hydrogen iodide is 1 to 1000 ppm on the basis of weight;*

*wherein the ratio of the methanol source (in terms of methanol) in the liquid object is not less than 80 mol relative to 1 mol of hydrogen iodide; and*

*wherein, in the decanter, the concentration of the methanol source in the upper layer portion of the condensed overhead (3A) is 0.3 to 50% by weight, the concentration of the methanol source in the lower layer portion of the condensed overhead (3A) is 0.1 to 20% by weight, the concentration of methyl iodide in the upper layer portion is 1 to 6% by weight, the concentration of methyl iodide in the lower layer portion is 60 to 95% by weight, and the concentrations of hydrogen iodide in the upper layer portion and in the lower layer portion are 1 to 300 ppm on the basis of weight.*

*14. The process according to claim 13, wherein the concentration of the methanol source in the liquid object is 2 to 40% by weight.*

*15. The process according to claim 13, wherein the concentration of the methanol source in the liquid object is 2 to 25% by weight.*

*16. The process according to claim 13, wherein, in the liquid object, the concentration of acetic acid is 0.3 to 50% by weight, and the ratio of the methanol source (in terms of methanol) is 0.1 to 40 mol relative to 1 mol of a total amount of acetic acid and hydrogen iodide.*

*17. The process according to claim 13, wherein, in the liquid object, the concentration of acetic acid is 0.5 to 50% by weight, the concentration of hydrogen iodide is 5 to 1000 ppm, and the ratio of the methanol source (in terms of methanol) is 1 to 20 mol relative to 1 mol of a total amount of acetic acid and hydrogen iodide.*

*18. The process according to claim 13, wherein the material of the acetaldehyde distillation column comprises an iron-based alloy.*

*19. The process according to claim 13, wherein the material of the acetaldehyde distillation column comprises a stainless steel or a two-phase stainless steel.*

*20. The process according to claim 13, wherein the material of the acetaldehyde distillation column comprises a nickel-based alloy.*

* * * * *